United States Patent [19]
Benner et al.

[11] Patent Number: 5,516,678
[45] Date of Patent: May 14, 1996

[54] METHOD FOR PRODUCING THE SSPI RESTRICTION ENDONUCLEASE AND METHYLASE

[75] Inventors: Jack S. Benner, Hamilton, Mass.; Linda H. Coe, Newton, N.H.

[73] Assignee: New England Biolabs, Inc., Beverly, Mass.

[21] Appl. No.: 319,621

[22] Filed: Oct. 6, 1994

[51] Int. Cl.⁶ ............... C12N 9/22; C12N 15/55
[52] U.S. Cl. .......... 435/194; 435/193; 435/252.33; 435/320.1; 536/23.2
[58] Field of Search .................. 435/199, 193, 435/320.1, 252.33; 536/232

[56] References Cited

FOREIGN PATENT DOCUMENTS 0193413  9/1986  European Pat. Off. .

OTHER PUBLICATIONS

Mann, et al., Gene 3:97–112 (1978).
Kosykh, et al., Molec. Gen. Genet.; 178:717–719 (1980).
Walder, et al., Proc. Natl. Acad. Sci, USA 78:1503–1507 (1981).
Bougueleret, et al., Nucleic Acids Res. 12:3659–3676 (1984).
Gingeras and Brooks, Proc. Natl. Acad. Sci USA, 80:402–406 (1983).
Theriault and Roy, Gene, 19:355–359 (1982).
Blumenthal, et al., J. Bacteriol, 164:501–509 (1985).
Kiss, et al., Nucl. Acids Res., 13:6403–6421 (1985).
Szomolanyi, et al., Gene, 10:219–225 (1980).
Janulaitis, et al., Gene, 20:197–204 (1982).
Kiss and Baldauf, Gene, 21:111–119 (1983).
Walder, et al., J. Bio. Chem., 258:1235–1241 (1983).
Lunnen, et al., Gene, 74:25–32 (1988).
Wilson, et al., Gene, 74:281–289 (1988).
Piekarowicz, et al., Nucleic Acids Res. 19:1831–135 (1991).
Piekarowicz, et al., J. Bacteriology, 173:150–155 (1991).
Fomenkov, et al., Nucl. Acids Res. 22:2399–2403 (1994).
Raleigh and Wilson, Proc. Natl. Acad. Sci. USA, 83:9070–9074 (1986).
Heitman and Model., J. Bact. 169:3243–3250 (1987).
Raleigh and Trimarchi and Revel, Genetics, 122:279–296 (1989).
Waite–Rees, et al., J. Bacteriology, 173:5207–5219 (1991).

*Primary Examiner*—Charles L. Patterson, Jr.
*Attorney, Agent, or Firm*—Gregory D. Williams

[57] ABSTRACT

The present invention is directed to a method for cloning and producing the SspI restriction endonuclease by 1) introducing the restriction endonuclease gene from Sphaerotilus species into a host whereby the restriction gene is expressed; 2) fermenting the host which contains the vector encoding and expressing the SspI restriction endonuclease, and 3) purifying the SspI restriction endonuclease from the fermented host which contains the vector encoding and expressing the SspI restriction endonuclease activity.

7 Claims, 16 Drawing Sheets

Ssp I genomic DNA
digested with Bgl II pBIISp 1.2 cut with Bgl II
and dephosphorylated Mix and ligate for 18 hours
Plate on media containing
ampicillin Scraped cells to make a primary CsCl-purified
plasmid library, selected library with Ssp I
endonuclease and plated selected library on
media containing ampicillin Picked 18 colonies, grew
10 ml overnight cultures
in LB/ampicillin and
miniprepped plasmid DNA Digested miniprep DNA with Ssp I and looked for
plasmids with insert DNA that were also
resistant to Ssp I cleavage Identified a 9.6 Kb Bgl II fragment
that was resistant to Ssp I cleavage

FIG. 1

```
     GGATCTCTATCGCGCAAAGTCAAAGGAAGAAGATATCACGGTTGAGAACGAAATCACAAA
  1  ------+---------+---------+---------+---------+---------+   60
      D  L  Y  R  A  K  S  K  E  E  D  I  T  V  E  N  E  I  T  K

GGAAAAATTCCCCATCAGCCTCAAGGCTTATGGGATGGTCCACTACAGCTTTCAACTGA
 61  ------+---------+---------+---------+---------+---------+  120
      E  K  F  P  I  S  L  K  A  Y  G  D  G  P  L  Q  L  S  T  D

CAAAAATTTTTGATGTACCCTCTTCTTGAGGAAATTGGGGCGTTCATCAATGCCAAAGA
121  ------+---------+---------+---------+---------+---------+  180
      K  N  F  L  M  Y  P  L  L  E  E  I  G  A  F  I  N  A  K  E

AAAAATAGAAGAAATTTTTGCCAATGAAGCATTTTCGTGCTTCAGCGAAATAAATGTCCT
181  ------+---------+---------+---------+---------+---------+  240
      K  I  E  E  I  F  A  N  E  A  F  S  C  F  S  E  I  N  V  L

ACCCTTGATATACGATGAGAAGAGGCAGCGATGTAATATTTTGGTTTTCGATGCCGCACG
241  ------+---------+---------+---------+---------+---------+  300
      P  L  I  Y  D  E  K  R  Q  R  C  N  I  L  V  F  D  A  A  R

TGCCAGAGCTGAAACAGCTTACATTCGCAAAGAAACAGAGGGTCAGGACGAAAACACCC
301  ------+---------+---------+---------+---------+---------+  360
      A  R  A  E  T  A  Y  I  R  K  E  T  E  G  S  G  R  K  H  P

GGCTTACAGATTTTTTGACAAAAATAAAAATTACATCTGCGAAGTGCGCTACGGGAATGC
361  ------+---------+---------+---------+---------+---------+  420
      A  Y  R  F  F  D  K  N  K  N  Y  I  C  E  V  R  Y  G  N  A

TGCGGCAAATGCGCTCCAACGAGACTTTGGACAAACACAAAAAATGCTACATCATTTTT
421  ------+---------+---------+---------+---------+---------+  480
      A  A  N  A  L  Q  R  G  L  W  T  N  T  K  N  A  T  S  F  F
```

FIG. 3A

```
          TGATAGTGTAACAAACGGCTGGGTTGATTACTCTCATAACTTGGTCTTAGTTAAGCTGCT
481       ------+---------+---------+---------+---------+---------+ 540
      b    D  S  V  T  N  G  W  V  D  Y  S  H  N  L  V  L  V  K  L  L

TTCGCACGCTTTGGTTTCAAGTCGCAAAGGCCACGAAGCTGCACTGGAAGAGATCAAGAA
541       ------+---------+---------+---------+---------+---------+ 600
      b    S  H  A  L  V  S  S  R  K  G  H  E  A  A  L  E  E  I  K  K

AGACATCCTGCAACTAAAGCAAACGAATGGGATCAATGTTTAACACCACACAACCATTGT
601       ------+---------+---------+---------+---------+---------+ 660
      b    D  I  L  Q  L  K  Q  T  N  G  I  N  V  *
      c                *  S  K  R  M  G  S  M  F  N  T  T  Q  P  L  F

TTGAAAAAGTAATTTTAGACACTCCGGAAACTCAAGGAATAAAATATGCCGGATCAAAAC
661       ------+---------+---------+---------+---------+---------+ 720
      c    E  K  V  I  L  D  T  P  E  T  Q  G  I  K  Y  A  G  S  K  L

TAAAATTGATCCAACACATTTTATCCCTACTAGGGTCTCGCAGGCCTTGGCGAAGTGCGA
721       ------+---------+---------+---------+---------+---------+ 780
      c    K  L  I  Q  H  I  L  S  L  L  D  N  L  D  V  K  T  V  F  D

ATGGGATTTCTGGAACTACTAGGTCTCAGATTGGTCTTATGTGTATTTGGCTTGTGCTTG...CGAAGTGCCGATTCATGTCA
781       ------+---------+---------+---------+---------+---------+ 840
      c    G  F  S  G  T  T  R  V  S  Q  A  L  A  K  C  G  F  H  V  T

CCAGCAACGACATTTCAGATTGGTCTTATGTGTATTTGGCTTGTGCTACCTAAAAAACAAAA
841       ------+---------+---------+---------+---------+---------+ 900
      c    S  N  D  I  S  D  W  S  Y  V  F  G  L  C  Y  L  K  N  K  K

AACACCCCAACGAATACAAGGAACTAATTGAACACCTTAACTCAATAAATGGCTACGACG
901       ------+---------+---------+---------+---------+---------+ 960
      c    H  P  N  E  Y  K  E  L  I  E  H  L  N  S  I  N  G  Y  D  G

GTTGGTTCACTGAGAAGTATGGCGGCCTTGACTATTCAGGCAGTGCTATTCAACCTGACG
961       ------+---------+---------+---------+---------+---------+ 1020
      c    W  F  T  E  K  Y  G  G  L  D  Y  S  G  S  A  I  Q  P  D  G
```

FIG.3B

```
1021 GCACAAAAAAACCTTGGCAAGTCCACACAATACGCGGAAGCTAGATGGGATCCGCGACGAAA 1080
        T  K  K  P  W  Q  V  H  N  T  R  K  L  D  G  I  R  D  E  I

1081 TAGATTCATTATCACTGAATGAAACCGAAAAAGCCGTGCCCTTACCAGTTTAATTTTAG 1140
        D  S  L  N  E  T  E  K  A  V  A  L  T  S  L  I  L  A

1141 CAATGGACGAAGTCGACAACACACTTGGCCACTTCACTTCATACCTAAAAGAATGGTCCC 1200
        M  D  E  V  D  N  T  L  G  H  F  T  S  Y  L  K  E  W  S  P

1201 CTCGATCATTCAAAGAAATGCGAATGAAAATCCCAAAAATATTATTAACTCCGAAGACA 1260
        R  S  F  K  E  M  R  M  K  I  P  K  I  F  I  N  S  E  D  N

1261 ACCAAGTATTAAAAGGCGATATATTCGCATCAATGACTAACATCAATGTCGATTTTGCTT 1320
        Q  V  L  K  G  D  I  F  A  S  M  T  N  I  N  V  D  F  A  Y

1321 ACTTTGATCCACCTTACGGTTCAAACAACGAAAAGATGCCTCCTTCGCGAGTACGCTATG 1380
        F  D  P  P  Y  G  S  N  N  E  K  M  P  P  S  R  V  R  Y  A

1381 CATCGTATTATCATTTATGGACAACTATATGCAAGAATGATAAGCCGAGCATTTTCGGAG 1440
        S  Y  Y  H  L  W  T  T  I  C  K  N  D  K  P  S  I  F  G  A

1441 CCGCAGGCAGAAGATTAGATACATCAGATAAAATTGCAGCAACCGTTTTTGAAGAGTTTC 1500
        A  G  R  R  L  D  T  S  D  K  I  A  A  T  V  F  E  E  F  R

1501 GAAAAGATGATGATGGTAAATTTATTGCAGTTAAAGCAATTGATAAATTAATAAAAAACA 1560
        K  D  D  D  G  K  F  I  A  V  K  A  I  D  K  L  I  K  N  I
```

FIG. 3C

```
1561  TTCAAGCACGATATGTTGCCCTTTCCTACAGTTCGGCGGAAAAGCCACTGCCGAGGAGC
      ----+----+----+----+----+----+----+----+----+----+----+----+  1620
         Q  A  R  Y  V  A  L  S  Y  S  S  G  G  K  A  T  A  E  E  L

1621  TAGGCGAAATACTTAACCGCCACGGAAAATTATAAAACAATTGAAGTTGATCACAAGC
      ----+----+----+----+----+----+----+----+----+----+----+----+  1680
         G  E  I  L  N  R  H  G  K  I  I  K  T  I  E  V  D  H  K  R

1681  GAAATGTCATGGCAGAAATGAAGTGGACCAATGAAGTGGCTTAGGGATGCAGAAGAGCCAA
      ----+----+----+----+----+----+----+----+----+----+----+----+  1740
         N  V  M  A  E  M  K  W  T  N  E  W  L  R  D  A  E  E  P  N

1741  ATCGAGAGTTTATTTTTCTCATTGAAAAAAATTCCTAACTGGGTGGTCAAGCGAACGCCA
      ----+----+----+----+----+----+----+----+----+----+----+----+  1800
         R  E  F  I  F  L  I  E  K  N  S  *

1801  ACAAGGACCACGGCTTCGCCGTTTTTACGGTCCCTGTTGGTGCCATTCACTCGCTTCGCT
      ----+----+----+----+----+----+----+----+----+----+----+----+  1860

1861  CCTTCCGGAGCCGTGCTTGACACGGGCGATCGGCTTTGGCCTGGTGTCCGTGGCCGCCGTG
      ----+----+----+----+----+----+----+----+----+----+----+----+  1920

1921  GCGGCGGTGCTGTTTGGAAAATTTCTGCTCCGGGGTTGCTGGCCCGCATTGGCGCTGGGCGTA
      ----+----+----+----+----+----+----+----+----+----+----+----+  1980

1981  TTTGTTCGTCTGAAGCGCCACGAAGTCCTGAGCGCGTCTGCACGGACGCGTTGTTCTCGA
      ----+----+----+----+----+----+----+----+----+----+----+----+  2040

2041  TGTCGAACTGCGGGGCTCGAC
      ----+----+---  2061
```

FIG. 3D

Primer 136 =

CAATTTTAGTTTGGATCCGGCATATTTGGTACCTTGAGTTTCCGGAG

Primer 137 =

GTCCTAGACCCGGGCATATGTCBAAAGCMGCMTAYCAAGATTTTAA
  where V = A, C, or G; M = A or C; Y = C or T Using primers 136 and 137, on genomic DNA, a 900 bp PCR product was identified. This 900 bp region encoded the entire SspI endonuclease.

| LIBRARY | VECTOR | HOST CELL TYPE | PRE-PROTECTED? | |
|---|---|---|---|---|
| Bgl II | pBIISp1.2 | RR1 | no | |
| EcoRI | pBIISp1.2 | RR1 | no | |
| PstI | pBIISp1.2 | RR1 | no | |
| SphI | pBIISp1.2 | RR1 | no | |
| PstI | pUC 19 | RR1 | no | |
| SphI | pUC19 | RR1 | no | |
| PstI | pACYC177 | RR1 | no | |
| PstI | pACYC177 | RR1 | yes | (Δ EcoRV) |
| SphI | pACYC184 | ER1797 | yes | (Δ EcoRV) |
| PstI | pACYC177 | ER1797 | yes | (Δ EcoRV) |
| XhoI | pUC19 | RR1 | no | |
| XhoI | pACYC177 | ER1797 | yes | (pUC19 D2 M) |
| XhoI | pACYC177 | ER2252 | yes | (pSspM-A8 & B5) |
| SphI | pACYC184 | ER2252 | yes | (pSspM-A8 & B5) |

Bgl II library in pBIISp1.2 gave a 9Kb full length M clone
EcoRI library in pBII Sp1.2 gave a partial M clone RR1 = Mcr A+, McrBC+/−, mrr−
ER 1797 = Mcr A−, McrBC−, mrr−
ER 2252 = Mcr A−, Mcr BC−, mrr−

FIG. 9

Primer 137 = GCTCTAGACCCGGGCATATGTCVAAAGCMGCMTAYCAAGATTTTAA
where V=A, C, or G; M=A or C; Y=C or T

```
        primer 137
        ATGTCVAAAGCMGCMTAYCAAGATTTAA
A9      ATGTCCAAAGCAGCCTACCAAGATTTCACAAAAAGATTCTCCCTGCTAATAAAAAACAT
        |----+----|----+----|----+----|----+----|----+----|----+----|
         M  S  K  A  A  Y  Q  D  F  T  K  R  F  S  L  L  I  K  K  H A10     ATGTCCAAAGCAGCCTACCAAGATTTCACAAAAAGATTCTCCCTGCTAATAAAAAACAT
        |----+----|----+----|----+----|----+----|----+----|----+----|
         M  S  K  A  A  Y  Q  D  F  T  K  R  F  S  L  L  I  K  K  H A12     ATGTCCAAAGCAGCCTACCAAGATTTCACAAAAAGATTCTCCCTGCTAATAAAAAACAT
        |----+----|----+----|----+----|----+----|----+----|----+----|
         M  S  K  A  A  Y  Q  D  F  T  K  R  F  S  L  L  I  K  K  H B1      ATGTCCAAAGCAGCCTACCAAGATTTCACAAAAAGATTCTCCCTGCTAATAAAAAACAT
        |----+----|----+----|----+----|----+----|----+----|----+----|
         M  S  K  A  A  Y  Q  D  F  T  K  R  F  S  L  L  I  K  K  H
```

FIG. 10A

```
A9       CCAAACCTCATAACGATGACACTGAGCAACATTTCACAATGCGACTCATTGGCAACAAA
   61    ----+----|----+----|----+----|----+----|----+----|----+----
         P  N  L  I  T  M  T  L  S  N  I  F  T  M  R  L  I  G  N  K

A10      CCAAACCTCATAACGATGACACTGAGCAACATTTCACAATGCGACTCATTGGCAACAAA
   61    ----+----|----+----|----+----|----+----|----+----|----+----
         P  N  L  I  T  M  T  L  S  N  I  F  T  M  R  L  I  G  N  K

A12      CCAAACCTCATAACGATGACACTGAGCAACATTTCACAATGCGACTCATTGGCAACAAA
   61    ----+----|----+----|----+----|----+----|----+----|----+----
         P  N  L  I  T  M  T  L  S  N  I  F  T  M  R  L  I  G  N  K

B1       CCAAACCTCATAACGATGACACTGAGCAACATTTCACAATGCGACTCATTGGCAACAAA
   61    ----+----|----+----|----+----|----+----|----+----|----+----
         P  N  L  I  T  M  T  L  S  N  I  F  T  M  R  L  I  G  N  K
```

FIG. 10B

```
A9   ACCCACGGCGACTTGGCTGAGATTGCGATTAGCGAATTCATTAATCAGTACATGTATGAC
121  ---------+---------+---------+---------+---------+---------+
      T  H  G  D  L  A  E  I  A  I  S  E  F  I  N  Q  Y  M  Y  D

A10  ACCCACGGCGACTTGGCTGAGATTGCGATTCTCCGAATTCATTAATCAGTACATGTATGAC
121  ---------+---------+---------+---------+---------+---------+
      T  H  G  D  L  A  E  I  A  I  S  E  F  I  N  Q  Y  M  Y  D

A12  ACCCACGGCGACTTGGCTGAGATTGCGATTCTCCGAATTCATTAATCAGTACATGTATGAC
121  ---------+---------+---------+---------+---------+---------+
      T  H  G  D  L  A  E  I  A  I  S  E  F  I  N  Q  Y  M  Y  D

B1   ACCCACGGCGACTTGGCTGAGATTGCGATTCTCCGAATTCATTAATCAGTACATGTATGAC
121  ---------+---------+---------+---------+---------+---------+
      T  H  G  D  L  A  E  I  A  I  S  E  F  I  N  Q  Y  M  Y  D
```

FIG. 10C

```
A9   TTTAAGTCAATTCATGTCGGCAAAGATCT
181  ---------+---------+--------
      F  K  S  I  H  V  G  K  D

A10  TTTAAGTCAATTCATGTCGGCAAAGATCT
181  ---------+---------+--------
      F  K  S  I  H  V  G  K  D

A12  TTTAAGTCAATTCATGTCGGCAAAGATCT
181  ---------+---------+--------
      F  K  S  I  H  V  G  K  D

B1   TTTAAGTCAATTCATGTCGGCAAAGATCT
181  ---------+---------+--------
      F  K  S  I  H  V  G  K  D
```

FIG. 10D

Amino acid Sequence to mRNA (DNA) Sequence

| 1 letter code | G | A | V | L | I | S | T | D | N | E | Q | K | P | H | R | F | Y | W | C | M |
|---|---|---|---|---|---|---|---|---|---|---|---|---|---|---|---|---|---|---|---|---|
| 3 letter code | Gly | Ala | Val | Leu | Ile | Ser | Thr | Asp | Asn | Glu | Gln | Lys | Pro | His | Arg | Phe | Tyr | Trp | Cys | Met |
| mRNA 5' | GGA | GCA | GUA | CUA | AUA | UCA | ACA | GAC | AAC | GAA | CAA | AAA | CCA | CAC | CGA | UUC | UAC | UGG | UGC | AUG 3' |
|  | C | C | C | C | C | C | C | U | U | G | G | G | G | U | C | U | U |  | U |  |
|  | G | G | G | G | U | G | G |  |  |  |  |  | G |  | G |  |  |  |  |  |
|  | U | U | U | U |  | U | U |  |  |  |  |  | U |  | U |  |  |  |  |  |
|  |  |  |  | or |  | or |  |  |  |  |  |  |  |  | or |  |  |  |  |  |
|  |  |  |  | UUA |  | AGC |  |  |  |  |  |  |  |  | AGA |  |  |  |  |  |
|  |  |  |  | G |  | U |  |  |  |  |  |  |  |  | G |  |  |  |  |  |

Special signals     RNA              Amino Acid Special Sympls
                    UAA = Ochre      B = D or N
                    UAG = Amber      Z = E or Q
                    UGA = terminate Ambiguous nucleotide abbrevations
These abbreviations conform to the IUPAC-IUB standard abbreviations.

```
     A  C  G  U/T
U/T =           U    Uracil/Thymine
G   =        G       Guanine
K   =        G  U
C   =    C           Cytosine
Y   =    C      U    Pyrimidine
S   =    C   G
B   =    C   G  U
A   = A              Adenine
W   = A         U
R   = A      G       Purine
D   = A      G  U
```

FIG. 11

METHOD FOR PRODUCING THE SSPI RESTRICTION ENDONUCLEASE AND METHYLASE

BACKGROUND OF THE INVENTION

The present invention relates to recombinant DNA which encodes the SspI restriction endonuclease and modification methylase, and to the production of these enzymes from the recombinant DNA.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Over one hundred different restriction endonucleases have been identified among many hundreds of bacterial species that have been examined to date.

Bacteria usually possess only a small number restriction endonucleases per species. The endonucleases are named according to the bacteria from which they are derived. Thus, Sphaerotilus species (ATCC 13925), synthesizes a restriction endonuclease named SspI. This enzyme recognizes and cleaves the sequence AAT▼ATT.

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by binding to infecting DNA molecules and cleaving them each time that the recognition sequence occurs. The disintegration that results inactivates many of the infecting genes and renders the DNA susceptible to further degradation by exonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries' i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones (HhaII: Mann et al., *Gene* 3:97–112, (1978); EcoRII: Kosykh et al., *Molec. Gen. Genet* 178:717–719, (1980); PstI: Walder et al., *Proc. Nat. Acad. Sci. USA* 78:1503 –1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucleic Acids Res.* 12: 3659–3676, (1984); PaeR7: Gingeras and Brooks, *Proc. Natl. Acad. Sci. USA* 80:402–406, (1983); Theriault and Roy, *Gene* 19:355–359, (1982); PvuII: Blumenthal et al., *J. Bacteriol.* 164:501–509, (1985)).

A third approach, and one that is being used to clone a growing number of systems, involves selecting for an active methylase gene (see, e.g. EPO Publication No. 193, 413, published Sep. 3, 1986 and BsuRI: Kiss et al., *Nucleic Acids Res.* 13:6403–6421, (1985)). Since restriction and modification genes tend to be closely linked, clones containing both genes can often be isolated by selecting for just the one gene. Selection for methylation activity does not always yield a complete restriction-modification system however, but instead sometimes yields only the methylase gene (BspRI: Szomolanyi et al., *Gene* 10:219–225, (1980); BcnI: Janulaitis et al, *Gene* 20: 197–204 (1982); BsuRI: Kiss and Baldauf, *Gene* 21: 111–119, (1983); and MspI: Walder et al., *J. Biol. Chem.* 258: 1235–1241, (1983)). For an overall review of cloning restriction-modification systems, see e.g., Lunnen et al., *Gene* 74:25–32 (1988) and Wilson, G. G., *Gene* 74:281–285 (1988).

Another method for cloning methylase and endonuclease genes is based on a colorimetric assay for DNA damage. When screening for a methylase, the plasmid library is transformed into the host *E. coli* strain AP1-200. The expression of a methylase will induce the SOS response in an *E. coli* strain which is McrA+, McrBC+, or Mrr+. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restrictive temperature of the lacZ gene. Transformants encoding methylase genes are detected on LB agar plates containing X-gal as blue colonies. (Piekarowicz, et. al., *Nucleic Acids Res.* 19:1831–1835, (1991) and Piekarowicz, et.al. *J. Bacteriology* 173:150–155 (1991)). Likewise, the *E. coli* strain ER 1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Xu et.al. *Nucleic Acids Res.* 22:2399–2403 (1994))

A potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease. Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci., USA* 83:9070–9074, (1986)) or methylated adenine (Heitman and Model, *J. Bact.*, 169:3243–3250, (1987); Raleigh, Trimarchi, and Revel, *Genetics*, 122:279–296, (1989) Waite-Rees, Keating, Moran. Slatko, Hornstra and Benner, *J. Bacteriology*, 173:5207–5219 (1991)). Cytosine-specific or adenine-specific methylase genes cannot be cloned easily into these strains, either on their own, or together with their corresponding endonuclease genes. To avoid this problem it is necessary to use mutant strains of *E. coli* (McrA$^-$ and McrB$^-$ or Mrr–) in which these systems are defective.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

The present invention relates to recombinant DNA which encodes the gene for the SspI restriction endonuclease and modification methylase from Sphaerotilus species (NEB strain #315, obtained from the American Type Culture Collection (ATCC) under the designation number #13925), as well as to related methods for production of these enzymes from the recombinant DNA. This invention also relates to a transformed host which expresses the restriction endonuclease SspI, an enzyme which recognizes the DNA sequence AAT▼ATT and cleaves as indicated between the first 5' T and third 5' A by the arrow the disclosure of which is hereby incorporated by reference herein.

The preferred method for cloning SspI comprises forming a sufficient number of libraries containing DNA express the corresponding methylase gene by incubating the library DNA with an appropriate restriction endonuclease, i.e. an enzyme that cleaves its recognition sequence when it is not methylated; and retransforming a host with recombinant DNA which has not been cleaved by being incubated with the restriction endonuclease and screening the resulting transformants for positive clones among survivors.

After constructing several libraries of Sphaerotilus species DNA, however, we were only able to obtain the methylase or parts of the methylase gene and part of the endonuclease gene, but never the entire endonuclease gene. This led to an alternative strategy for cloning the SspI endonuclease gene. This strategy involved cloning the endonuclease gene directly under control of the $T_7$ promotor system in the vector pAII17 with no methylase present in the host cell.

BRIEF DESCRIPTION OF THE DRAWINGS

FIG. 1 illustrates the scheme for cloning the SspI restriction methylase.

FIG. 3 is the DNA sequence (SEQ ID No: 11 and SEQ ID NO: 13) and corresponding amino acid sequence (SEQ ID NO: 12) for the C-terminal portion of the endonuclease and amino acid sequence (SEQ ID NO: 14) for entire methylase of the BglII-XhoI methylase subclone.

FIG. 7 is a map of where the PCR primers used to directly amplify the endonuclease gene were derived from.

FIG. 9 is a table of different libraries prepared.

FIG. 10 is the DNA sequence and corresponding amino acid sequence (A 9=SEQ ID NO: 15, SEQ ID NO: 16; A 10 =SEQ ID N: 17, SEQ ID NO: 18; A 12 =SEQ ID NO: 19, SEQ ID NO: 20, and B 1 =SEQ ID NO: 21, and SEQ ID NO:22) of four different clones with SspI activity.

FIG. 11 is an explanation of the one letter code for amino acid sequence.

DETAILED DESCRIPTION OF THE INVENTION

The present invention relates to recombinant DNA which encodes the SspI restriction endonuclease and modification methylase, as well as to the enzymes produced from such a recombinant DNA.

Figure 6:
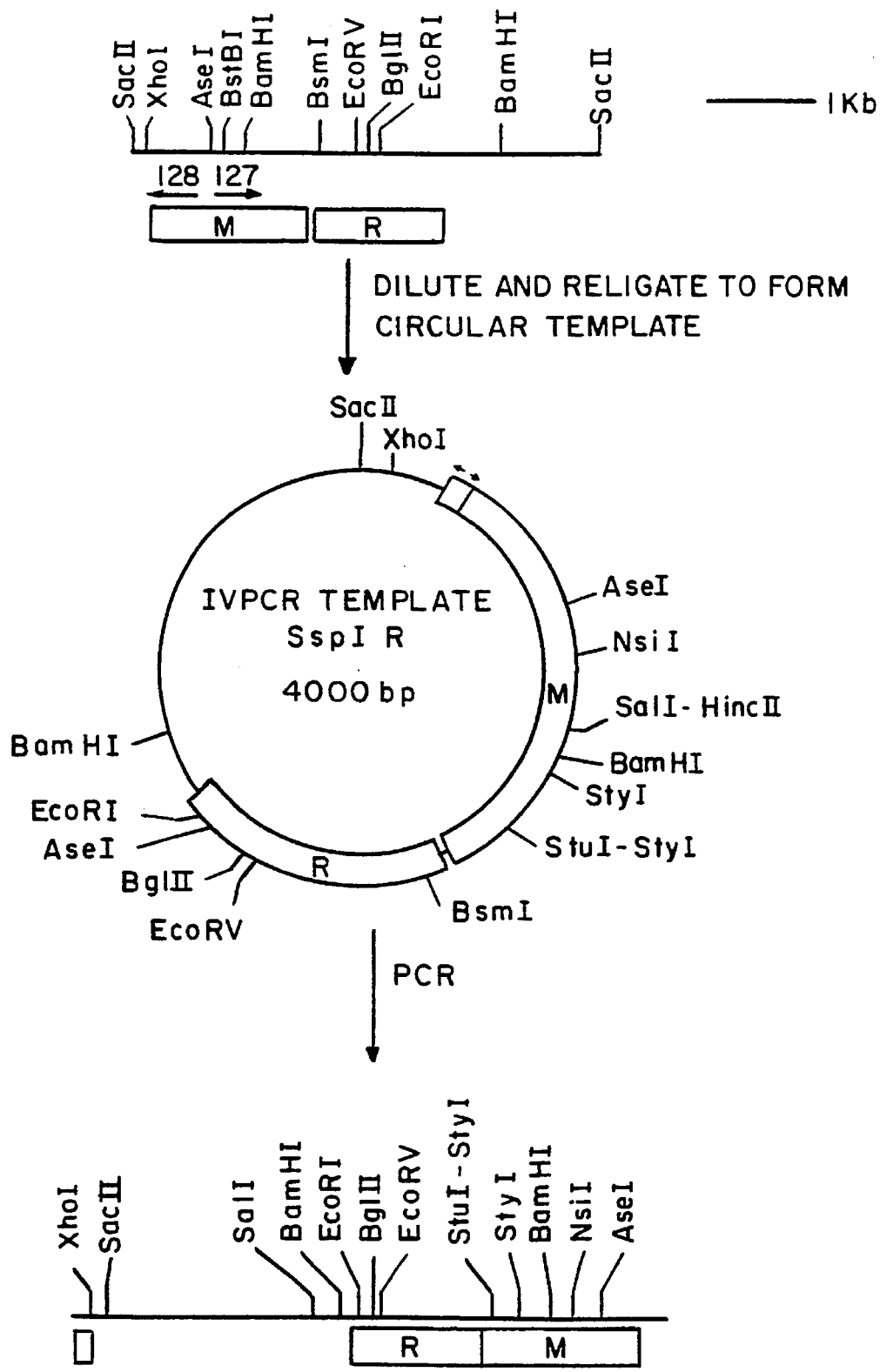
FIG. 6 is the scheme for inverse PCR on the SacII cut and religated genomic DNA.
Figure 7:
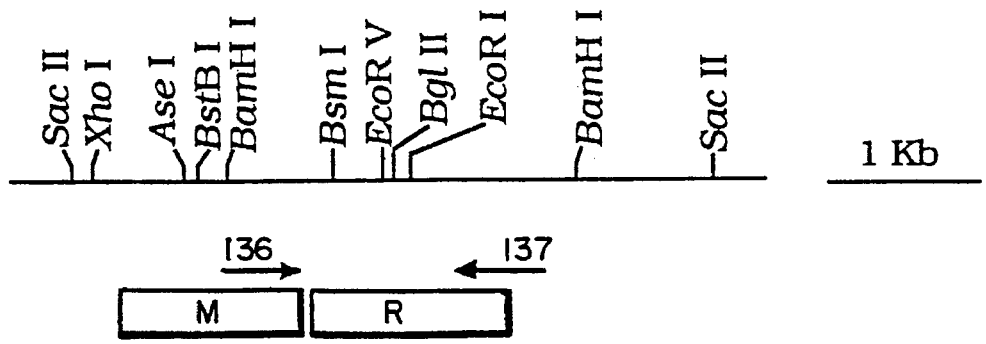

The method described herein by which the SspI restriction gene and methylase gene are preferably cloned and expressed is illustrated in FIGS. 1, 6 and 7 and includes the following steps:

I. Cloning the SspI methylase.

A. Preparation of Libraries.

A-1. Sphaerotilus species is grown accordance with the standard protocols for growing Sphaerotilus species at New England Biolabs as described in detail in the Examples. The cells are lysed and the genomic DNA purified by the techniques described in Brooks, et al., *Nucleic Acids Research*, 17:979–997, (1989).

A-2. The genomic DNA is digested fully with the following restriction endonucleases: BglII, EcoRI, PstI, SphI, and XhoI.

A-3. These restriction enzyme fragments are ligated into a corresponding cloning site (e.g., BglII generated fragments are ligated into the BglII cloning site, and so on) of a cloning vector, ideally one that has one, or two SspI sites and the cloning site, such as pBIISpI.2, pUC19, pACYC177, or pACYC 184, and the mixture is used to transform an appropriate host cell such as *E. coli* RR1 cells which are Mrr$^-$or any other *E. coli* strain which is Mrr$^-$and/or McrA$^-$.

A-4. The transformed mixture is plated onto media selective for transformed cells, such as the antibiotics ampicillin, tetracycline, kanamycin or chloramphenicol. After incubation, the transformed colonies are collected together into a single culture, the cell library.

A-5. The recombinant plasmids are purified in toto from the cell library to make the plasmid library.

B. Selection and Screening of the Libraries.

B-1. The plasmid library is digested to completion in vitro with the SspI restriction endonuclease, prepared from Sphaerotilus species, by a method similar to that described in Watson et al, supra. SspI digestion differentially destroys unmodified, non-methylase-containing, clones, increasing the relative frequency of SspI methylase clones.

B-2. The selected DNA is transformed back into an appropriate host such as *E. coli* RR1, and transformants are recovered by plating onto selective media. The colonies are picked and their DNA is analyzed for the presence of the SspI modification gene: the plasmids that they carry are purified and incubated with the SspI restriction endonuclease to determine whether they are resistant to digestion. Total cellular DNA (chromosomal and plasmid) is also purified and incubated with the SspI restriction endonuclease. The DNA of clones that carry the SspI modification gene should be fully modified, and both plasmid DNA and total DNA should be substantially resistant to digestion.

B-3. The DNA libraries generated, such as EcoRI, PstI, SphI and XhoI are prepared for Southern blotting and probed with the cloned methylase gene, such as pSspIM14.0B 6.

C Mapping of the modification methylase gene and preparation of deletion subclones.

Figure 2:
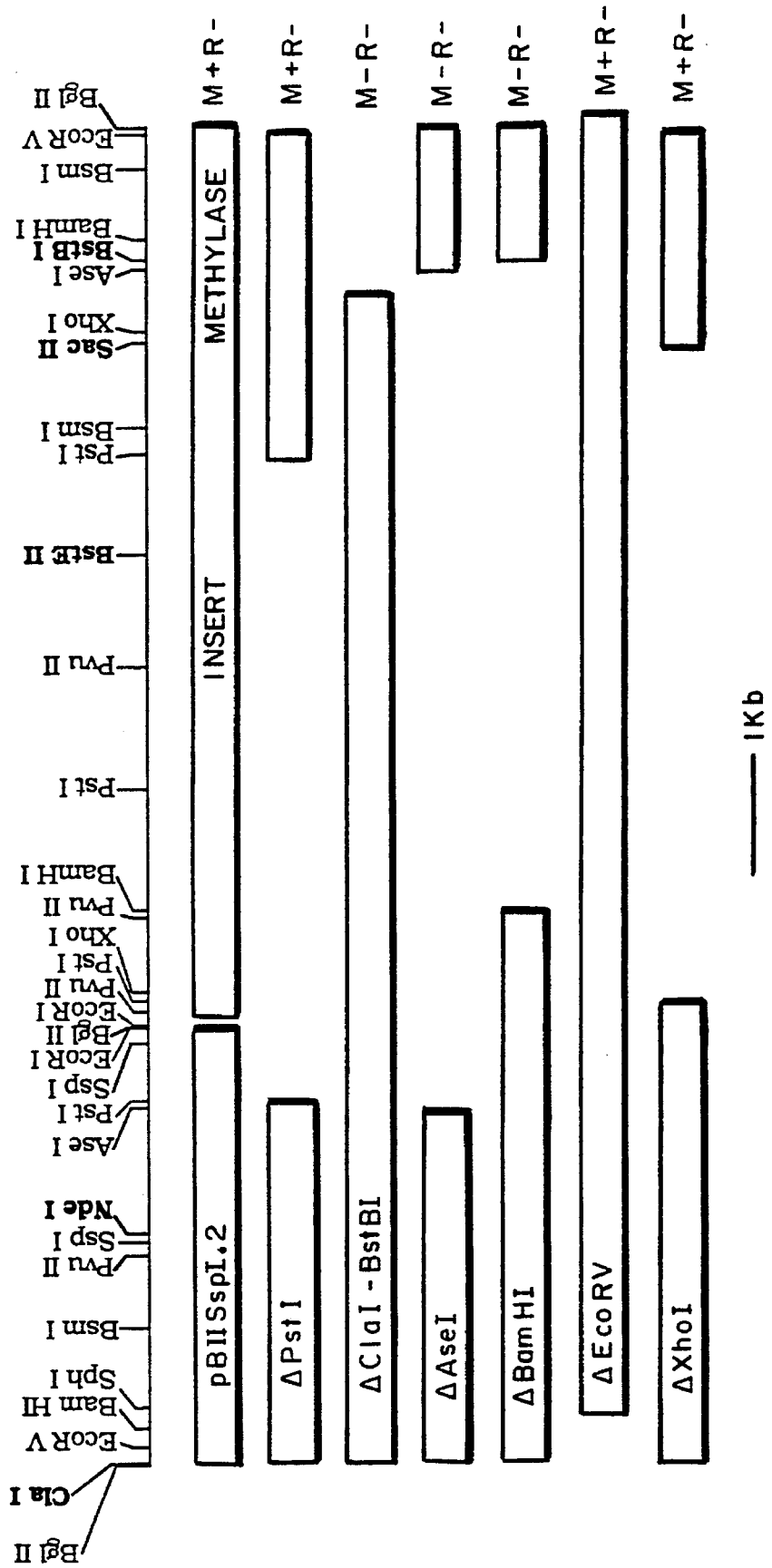
FIG. 2 is a restriction map of the 9.6 Kb BglII fragment that encodes the SspI methylase with the deletions of the BglII clone.

C-1. The SspI methylase clone pSspIM14.0-B6 was mapped with a number of different restriction enzymes. The restriction map appears in FIG. 2.

C-2. The SspI methylase clone pSspIM14.0-B6 was digested with the following restriction enzymes: PstI, AseI, BamHI, EcoRV, and XhoI; and religated. These deletion subclones were assayed for methylase activity by subjecting them to digestion with SspI and screening for survivors. Some of these deletion subclones had methylase activity, others had no methylase activity. This demarked an area of about 1.2 kilobases in length which was the putative methylase gene (see FIG. 2).This area was between the XhoI site and the BglII site. pSspIM14.0-b 6 was digested with BglII and XhoI. This fragment was subcloned into the SalI to BamHI site on pUC18 and in pUC19.

C-3. The smallest methylase subclone, a 1.2 Kb BglII to XhoI fragment, was subjected to DNA sequencing. The DNA sequence of this region appears in FIG. 3.

D. Preparation of SspI Endonuclease Protein, Protein Sequencing the SspI Endonuclease, and Mapping the Location of the Endonuclease.

Figure 4:
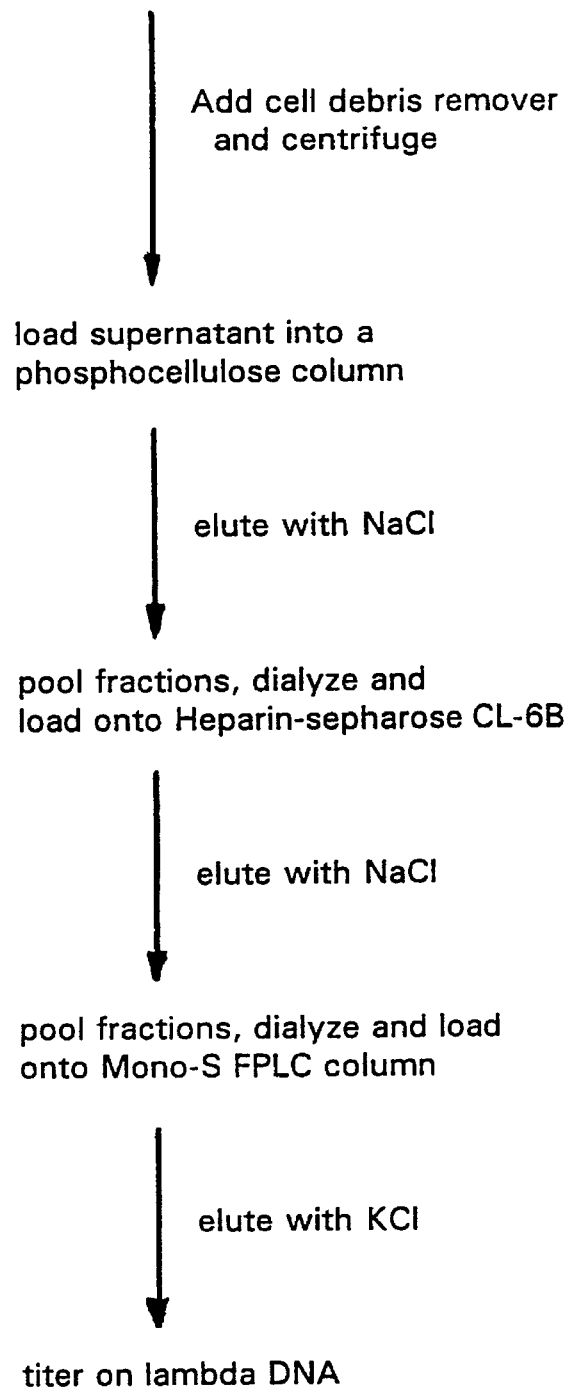
FIG. 4 illustrates the scheme for producing the SspI restriction endonuclease.

DC-1. The SspI restriction endonuclease is produced from Sphaerotilus species cells carrying the SspI restriction and modification genes. The cells are propagated in a fermenter in a rich medium. The cells are harvested by centrifugation. The cells are disrupted by a gaulin mill to produce crude cell extract containing the SspI restriction endonuclease activity. The crude cell extract containing the SspI restriction endonuclease activity is purified by standard ion-exchange and affinity chromatography techniques. FIG. 4 illustrates the scheme for producing the SspI restriction endonuclease.

D-2. The endonuclease so purified is homogeneous on SDS polyacrylamide gel electrophoresis and has an apparent molecular weight of 32,000 daltons and a specific activity of approximately 140,000 units/mg (or more) of protein titered on lambda DNA.

DC-3. The amino terminal sequence of the endonuclease is obtained using an Applied Biosystems 470A Protein Sequencer (Brooks, et al., *Nucleic Acids Research,* 17:979–997, (1989)), and a DNA oligonucleotide probe is made based on the protein sequence.

Figure 5:
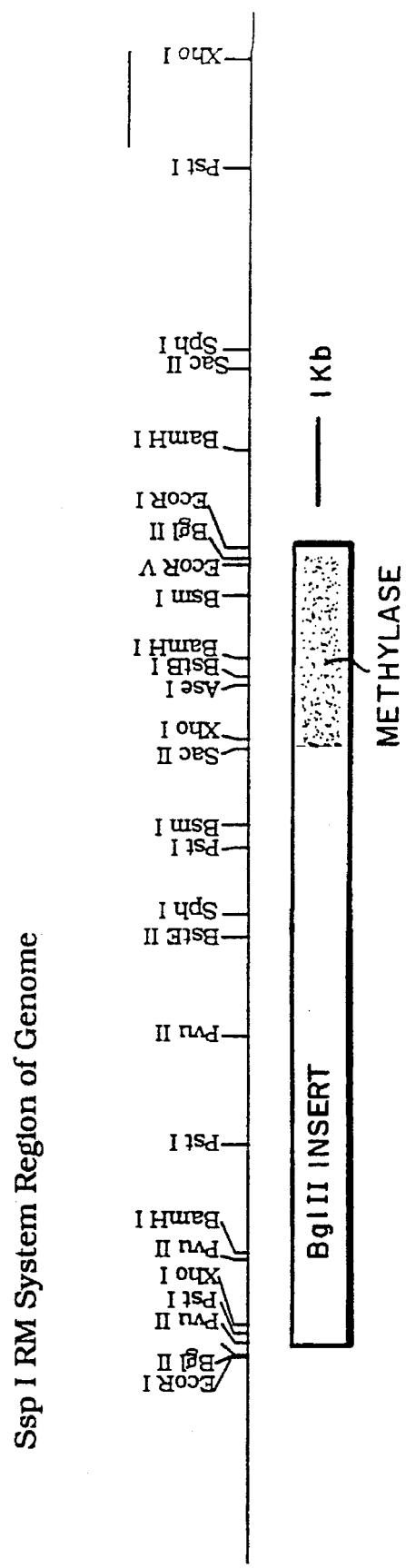
FIG. 5 is a map of the Sphaerotilus sp. genomic DNA in the region of the methylase and endonuclease genes.

DC-4. The probe is used to map the location of the endonuclease relative to the methylase clone in the Sphaerotilus species genome. FIG. 5 illustrates the methylase and endonuclease genes in the Sphaerotilus species genome.

II. Cloning the SspI Endonuclease Gene

A. Construction of new libraries in an McrA⁻ pre-protected host.

A-1. Based on the DNA sequence of the methylase, one can design primers specifically for cloning the SspI methylase gene. Two PCR primers were designed. The SspI methylase was amplified from pSspIM14.0-B6 and subcloned into the polylinker of pUC18 and pUC19 so that the direction of the methylase gene was running with the lac promotor in the pUC18 construct (construct pSspM-B5) and against the lac promotor in the pUC19 construct (construct pSspM-A8).

A-2. New SphI and XhoI libraries were made in pACYC184. These libraries were transformed into an McrA⁻ host (ER1797) pre-protected overexpressed methylase constructs, pSspM-B5 or pSspM-A8. These libraries were prepared for Southern blotting and were probed with an oligomer specific for the endonuclease gene. There was no detectable SspI restriction endonuclease gene in any of these libraries.

B. Inverted PCR of SspI genomic DNA

B-1. A template for inverted PCR of the SspI endonuclease gene was prepared by doing a limit digest of SspI genomic DNA with SacII. The target SacII fragment is about 4 kb in length and should encode the entire methylase and endonuclease gene. After digestion, the DNA was diluted out and religated to form a circular template.

B-2. PCR primers were designed which flanked the AseI site in the methylase gene. Amplification was performed and the expected 4 kb product was identified. FIG. 6 illustrates the scheme for doing inverse PCR on the genomic template.

B-3. The 4 kb PCR product was random primed and used to probe a Southern blot of Sphaerotilus genomic DNA. The PCR product was determined to map to the location of the endonuclease.

B-4. Attempts to clone the inverse PCR product into competent ER 2252 cells pre-protected with the pSspM-A8 or pSspM-B5 methylase construct failed.

B-5. The inverse PCR product was cut with BglII and XhoI to isolate the N-terminal half of the endonuclease gene. This product was cloned into the BamHI to SalI site on pUC19.

B-6. The BglII-XhoI fragment of the inverse PCR product was mapped with EcoRI, SacII, BamHI and SalI and determined to have the correct structure to be the N-terminal half of the SspI endonuclease gene. This N-terminal portion of the endonuclease gene could be added to the C-terminal portion already cloned to obtain a fully functional endonuclease.

C. Using PCR to amplify the restriction endonuclease gene.

C-1. Primers for PCR were designed for the N-terminal and C-terminal ends of the SspI endonuclease. The degenerate primer for the N-terminal was based on the protein sequence obtained for the SspI endonuclease with an NdeI site engineered in. The primer for the C-terminal was based on DNA sequence of the modification methylase with a BamHI site engineered in. FIG. 7 illustrates where the primers for amplifying the endonuclease gene were derived from.

C-2. Amplification was performed on the Sphaerotilus species genomic template with the primers from C-1 using Vent DNA polymerase in the presence of dNTP's and MgSO$_4$.

D. Cloning the PCR product into the vector pAII17.

DC-1. The 900 base pair PCR product was cloned into the NdeI to BamHI site on the vector pAII17. The plasmid pAII17 is a T$_7$ vector based on pET 11c. (Kong, et al. *Journal of Biological Chemistry*, 268: 1965–19 75, (1993)) The ligation was transformed into both *E. coli* RR1 and ER 2169. Neither cell strain was pre-protected with the SspI methylase.

Figure 8:
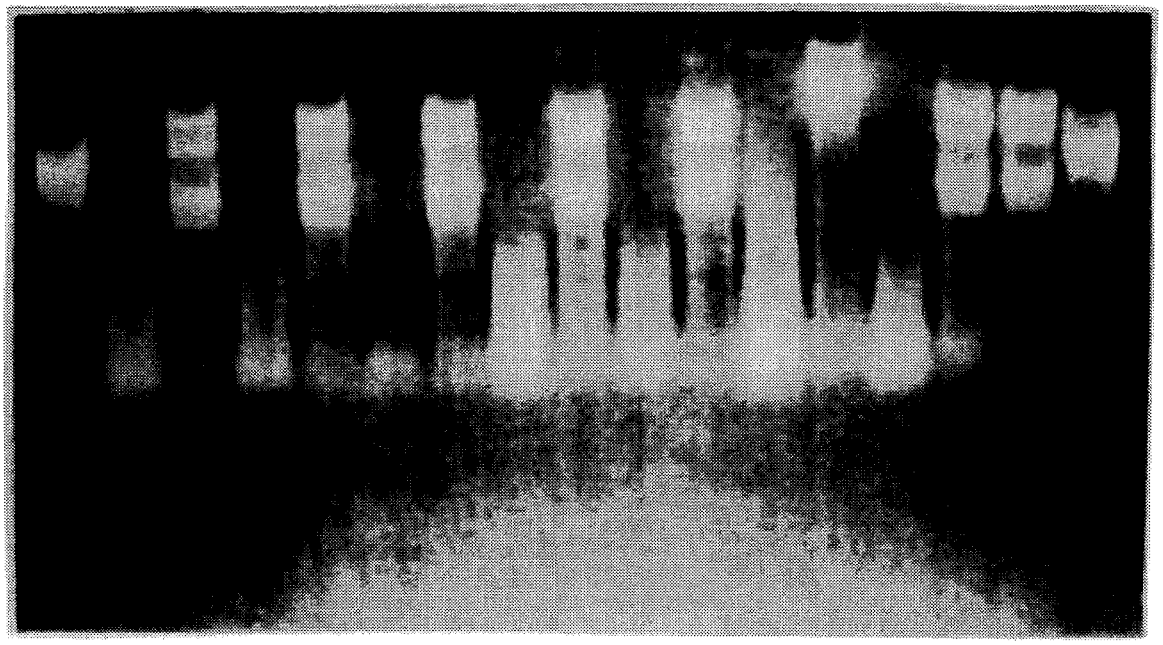
FIG. 8 is a photograph of an agarose gel demonstrating SspI restriction endonuclease activity in cell extracts of *E. coli* ER 2169 carrying the endonuclease gene in the plasmid pAII17.

DC-2. Ninety-six colonies of ER 2169 transformants were picked and replated on L-agar ampicillin plates and L-agar, ampicillin with 10 mM IPTG plates. Colonies corresponding to those which did not grow in the presence of IPTG were grown individually and induced with 10 mM IPTG. The crude cell extracts were assayed for SspI activity on lambda DNA. FIG. 8 is a photograph of SspI activity in the crude cell extracts as assayed on lambda DNA.

Although the above-outlined steps represent the preferred mode for practicing the present invention, it will be apparent to those skilled in the art that the above-described approach can vary in accordance with techniques known in the art.

The following Example is given to illustrate embodiments of the present invention as it is presently preferred to practice. It will be understood that this example is illustrative, and that the invention is not to be considered as restricted thereto except as indicated in the appended claims.

EXAMPLE

CLONING OF SspI RESTRICTION ENDONUCLEASE GENE

I. Cloning the SspI Methylase.

A. Preparation of Libraries.

A-1. Genomic DNA purification: Approximately five grams of Sphaerotilus species cells (ATCC #13925) were thawed and resuspended in 0.1M Tris-HCl, pH 7.1, 0.1M ETDA (25 ml) in a Corning plastic tube (50 ml). A solution of 60 mg of lysozyme in 35 ml of the above buffer was divided into two 50 ml plastic tubes and equal portions (15 ml) of the cell suspension added to each. The solutions were incubated at 37° C. for fifteen minutes. SDS was added from a 20% stock solution to adjust the final concentration of SDS to 1%. 200 ul of Proteinase K (20 mg/ml stock) was added and incubated for one hour at 37° C. The solution appeared stringy and diffuse at this point but was not clear. Two mls of 10% SDS/ 8% sarcosyl was added to the tubes (1 ml each) and heated at 55° C. for two hours. The sample remained stringy but not totally cleared. The samples were dialyzed against TE (10 mM Tris-HCl, pH 7.1, 1 mM EDTA) (2 L) with a single change—total 16 hours. After dialysis the solution (98 ml) was prepared for CsCl gradients by dilution with an equal vol. of TE pH 8.0, divided into two portions and to each an addition of 98.0 g of CsCl and 1 ml of a 5 mg/ml Ethidium bromide was made. The twenty tubes were spun in the Ti70 rotor for 48 hrs at 44,000 rpm. The bands were removed and extracted with CsCl-water-saturated isopropanol. The solution was dialyzed against the same buffer (4 L) as before and then phenol and chloroform extracted (one time each). This solution was dialyzed once again to remove phenol and then subjected to electrophoresis.

A-2. Limit digestion: The purified DNA was cut with BglII, to achieve total digestion as follows: 300 ul of DNA at 100 ug/ml in 50 mM Tris pH 7.5, 10 mM MgCl$_2$, 100 mM NaCl, 1 mM DTT buffer was dispensed into three tubes. To the tube was added 50 units of the appropriate restriction enzyme. The tubes were incubated at 37° C. for one hour, then phenol/chloroform extracted and ethanol precipitated. The pellets were redissolved in 300 ul of 10 mM Tris-HCl, 1 mM EDTA, pH 8.0 and 10 ul from each analyzed by agarose gel electrophoresis.

A-3. Ligation: The fragmented DNA was ligated to pBI-ISp1.2 (pBII 01 (ATCC #67901) cut with XcaI and a linker with an SspI site inserted) as follows: 10.0 ug of BglII digested Sphaerotilis species DNA (100 ul) was mixed with 2.0 ug BglII-cleaved and dephosphorylated pBIISp 1.2 (20.0 ul) and ethanol precipitated. The DNA was centrifuged at 12,000 g, 4° C. for 15 minutes and washed once with 100 ul 70% ethanol. The DNA was resuspended in 99 ul of 1 X ligation buffer (50 mM Tris, pH 7.5, 10 mM MgCl$_2$ 10 mM DTT, 0.5 mM ATP), 1 ul of T 4 DNA ligase was added and the mixture allowed to incubate at 16° C. for 16 hours. Aliquots of 3 ul were used to transform *E. coli* strain RR1 as follows. Each aliquot was mixed with 200 ul of ice-cold competent *E. coli* RR1 cells and placed on ice for thirty minutes. After a 2-minute heat shock at 42° C., the cells were diluted with one ml of Luria-broth (L-broth) and grown for one hour at 37° C.

A-4. Primary Cell Libraries: The transformed cell cultures were centrifuged, resuspended in 250 ul volumes and plated onto Luria-agar (L-agar) plates containing 100 ug/ml ampicillin. After overnight incubation at 37° C., the plates were removed and the approximately 114,000 colonies scraped-up into 25 ml of LB with antibiotic. Plasmid DNA was prepared from these cells as follows: the cells were pelleted by centrifugation and three grams of cell paste was resuspended in 14 ml of 25 mM Tris-HCl, 10 mM EDTA pH 8.0 and 50 mM glucose. The suspension was made 4.0 mg/ml in lysozyme and incubated at 25 degrees for 5 minutes. A 27 ml aliquot of 1% sodium dodecyl sulfate and 0.2N NaOH was added followed by mixing of the solution and incubation for 5 minutes at 0 degrees. Genomic DNA was precipitated by the addition of 20 ml of ice-cold 3M potassium acetate, pH 4.8, vortexed gently for 10 seconds, left on ice for 5 minutes and centrifuged at 12,000× g for ten minutes. The supernatant was removed and extracted with an equal volume of phenol/chloroform (1:1). The layers were separated by centrifugation at 10,000× g for 5 minutes. The upper layer was removed and extracted with an equal volume of chloroform. The layers were separated by centrifugation at 10,000× g for 5 minutes. The upper layer was removed and the nucleic acids precipitated by the addition of two volumes of ethanol. The precipitate was collected by centrifugation at 12,000× g for twenty minutes. The pellet was washed with 70% ethanol once and repelleted as before. The pellet was dried under vacuum and resuspended in 8 ml of 10 mM Tris-HCl, 1 mM EDTA, pH 8.0. The DNA solution was prepared for cesium chloride-ethidium bromide equilibrium density centrifugation by the addition of 8 grams of cesium chloride and 0.5 ml of a solution of ethidium bromide (5 mg/ml) were added. The DNA solution was centrifuged at 44,000 rpm for 48 hours and the resulting band of plasmid DNA was removed with a syringe and 18 g needle. The ethidium bromide was removed by extracting with an equal volume of CsCl-water-saturated isopropanol. The cesium chloride was removed by dialysis. The DNA was extracted with an equal volume of phenol/chloroform (1:1), and dialyzed against 10 mM Tris-HCl, 1 mM EDTA, pH 8.0, overnight.

B. Selection and Screening of the Libraries.

B-1. Primary Selection and Selected Library: 1 ug (12.0 ul) of the BglII plasmid library was diluted into 27 ul of restriction endonuclease digestion buffer (10 mM Tris pH 7.5, 10 mM MgCl$_2$, 1 mM DTT, 50 mM NaCl and 100 ug of bovine serum albumin). 100 units (1 ul) of SspI restriction endonuclease was added and the tube was incubated at 37° C. for 2 hours, at which time 7 U (1 ul) of calf intenstinal phosphatase was added and the reaction was incubated for an additional 30 minutes. 5 ul aliquots of this reaction mixture were mixed with 200 ul of ice-cold competent *E. coli* RR1 cells and transformed, plated and grown overnight as for the primary library.

B-2. Analysis of individuals: Colonies from the above transformation were picked and plated on LB agar plates containing ampicillin. Eighteen colonies were grown up in 10 ml cultures and the plasmids that they carried were prepared by the following miniprep purification procedure, adapted from the method of Birnboim and Doly (*Nucleic Acids Res.* 7:1513 (1979)).

Miniprep Procedure: Each culture was processed as follows: 1.5 mls of the overnight culture was pelleted at 6,000× g for 5 minutes. The supernatant was poured off and the cell pellet was resuspended in 150 ul of 25 mM Tris, 10 mM EDTA, 50 mM glucose, pH 8.0, containing 2 mg/ml lysozyme. After five minutes at room temperature, 200 ul of 0.2M NaOH, 1% SDS was added and the tube was shaken to lyse the cells, then placed on ice. After five minutes, 150 ul of 3M sodium acetate, pH 4.8, was added and shaken and placed on ice for an additional five minutes. The precipitate that formed was spun down at 12,000× g, at 4° C. for five minutes. The supernatant was removed and extracted with an equal volume of phenol/chloroform (1:1). The layers were separated by centrifugation at 10,000× g for five minutes. The supernatant was poured into a centrifuge tube containing 880 ul of ethanol and mixed. After 10 minutes at room temperature, the tube was spun at 12,000× g for 10 minutes to pellet the precipitated nucleic acids. The supernatant was discarded and the pellet was washed again with one ml of 70% ethanol-water, repelleted and dried at room temperature for 30 minutes under vacuum. Once dry, the pellet was resuspended in 50 ul of 10 mM Tris, 1 mM EDTA, pH 8.0 containing 20 ug/ml RNase and incubated for 1 hour at 37° C. to digest the RNA.

The plasmid minipreps were subsequently analyzed by digestion with SspI and BglII.

B-3. Methylase Gene Clones: 11% of the plasmids that were analyzed were found to be resistant to SspI and to carry a BglII fragment of approximately 9.6 Kb in length. These plasmids were subsequently shown to encode only a functional SspI modification methylase gene and not the restriction endonuclease gene. The other 89% of the plasmids looked at were not resistant to SspI and contained spurious fragments or were vector religated. No clones were found in the other four libraries, EcoRI, PstI, SphI and XhoI, that were resistant to cleavage by SspI endonuclease. These four libraries were prepared for Southern blotting as follows: 1 ug of the library DNA was digested with SspI, or the cloning enzyme (i.e., PstI for the PstI library, EcoRI for the EcoRI library, etc.) The digests were run with uncut library DNA and genomic DNA digested with the cloning enzyme on a 0.7% agarose gel overnight. The gel was washed in two changes of 0.25M HCl for 15 minutes, then in two changes of 0.5M NaOH, 1.5 M NaCl for 15 minutes each and finally in two changes of 1M NH$_4$OAc, 0.02M NaOH for 30 minutes. To transfer the DNA to nitrocellulose, a sheet of 0.45 um pore size nitrocellulose was wet in 1M NH$_4$OAc, 0.02M NaOH and a piece the same size as the gel was placed on either side of the gel. This was placed on top of a two inch high stack of paper towels and another two inch stack of paper towels was placed on top. A glass plate was placed on the top of the stack and a small weight was placed on top. The DNA transfer was allowed to proceed overnight. The nitrocellulose was baked at 80° C. for one hour. A $^{32}$P-labeled probe was prepared by nick translating the methylase clone pSspIM14.0-B6 as follows: 1 ug of pSspIM14.0-B6 was resuspended in 0.5M Tris-HCl, pH 7.8, 50 mM MgCl$_2$, 0.1M beta-mercaptoethanol, and 0.5 mg/ml BSA. 4 ul of each of a 0.1 mM dCTP, dGTP and dTTP were added along with 10 ul of 650 Ci/mmol $\alpha^{32}$-P dATP. Four picograms of DNAase I were added along with 10 units of *E. coli* DNA Polymerase I. This mixture was incubated for three hours at 16° C.

The nitrocellulose blot was pre hybridized in 15 mls of 50× Denhardt's (5 g ficoll, 5 g polyvinylpyrrolidone, 5 g BSA in 500 mls H$_2$O), 20× SSC (175.3 g NaCl, 88.2 g Sodium citrate in 1 L H$_2$O), 10% SDS and 10% dextran sulfate. After prehybridizing at room temperature for one hour, the labelled probe was added and the hybridization step was carried out at 68° C. overnight. The blot was washed in three changes of 2× SSC at 68° C. and three changes of 2× SSC with 0.1% SDS over the period of one hour. The blot was exposed to X-ray film for 4 and 18 hours.

Only the EcoRI library was found to contain a methylase clone which hybridized to the probe.

C. Mapping the SspI Methylase Clone and Preparation of Deletion Subclones.

C-1. 5 ug of pSspIM14.0-B6 were digested with PstI restriction endonuclease as follows: 50 ul of DNA at a concentration of 100 ug/1 ml in 50 mM Tris, pH7.9, 10 mM MgCl$_2$, 100 mM NaCl, 1 mM DTT was dispensed in one tube. To the tube, 100 units of PstI endonuclease was added and the reaction was incubated for 2 hours at 37° C. The whole digest was run out on a 0.7% agarose preparative gel. The fragment of choice, an approximately 7 kb PstI fragment, determined to contain the whole methylase gene, was cut out of the gel. The gel fragment was alternately extruded through a 21 gauge needle and frozen. This was repeated three times. The resultant mixture was centrifuged at 100, 000× g for 1 hour at 4° C. to pellet the agarose. The aqueous solution remaining was brought up to a NaCl concentration of 0.4M and precipitated with 2 volumes of isopropanol. The DNA was pelleted by centrifugation at 12,000× g for 20 minutes and washed once with cold 70% ethanol. The DNA pellet was resuspended in 2 ml TE (10 mM Tris, 1 mM EDTA, pH 8) and extracted with an equal volume of phenol. The layers were separated by centrifugation at 10,000× g for 10 minutes. The upper layer was removed and extracted with an equal volume of phenol/chloroform (1:1), and the layers were separated by centrifugation at 10,000× g for 10 minutes. The upper layer was removed and extracted with an equal volume of chloroform and centrifuged at 10,000× g to separate the layers. The aqueous layer was removed, and the DNA precipitated by the addition of ⅒ volume (0.2 ml) 2.75M sodium acetate and 2 volumes of cold ethanol. The DNA was pelleted by centrifuging at 12,000× g for 20 minutes and washed once with cold 70% ethanol. The DNA was resuspended in 0.5 ml TE (10 mM Tris, 1 mM EDTA, pH 8).

C-2. The gel prepped DNA fragments were religated in the following manner: 5 ul of 10× ligation buffer (50 mM Tris, pH7.5, 10 mM MgCl$_2$, 10 mM DTT, 0.5 mM ATP) was added to 45 ul of the gel prepped restriction digest fragment and 1 ul of T4 DNA Ligase was added and the mixture was allowed to incubate at 16° C. for 16 hours. Aliquots of 1, 2, and 3 ul were used to transform *E. coli* strain RRI as described in section I A-3. The transformed cell cultures were centrifuged, resuspended in 250 ul volumes and plated onto L-agar containing 15 ug/ml tetracycline. The cultures, now on plates, were incubated overnight at 37° C.

C-3. Several colonies were miniprepped as described in Section I (B-2) and were found to have the correct sized fragment. The PstI deletion clone was found to be resistant to SspI digestion and thus contained the entire methylase gene.

In the same manner described in I (C-1), pSspIM14.0B6 was also digested with AseI in 50 mM Tris-HCl, pH7.9, 10 mM MgCl$_2$, 100 mM NaCl 1 mM DTT then a 5 Kb digestion product was gel prepped, religated, and plated on 15 ug/ml tetracycline. Miniprepped DNA was then subjected to SspI digestion and were found to not be resistant to SspI. pSspIM14.0-B6 was also digested with BamHI in 10 mM Tris-HCl, pH 7.9, 10 mM MgCl$_2$, 150 mM NaCl, 1 mM DTT then a 7 Kb digestion product was gel prepped, religated, and plated on 100 ug/ml ampicillin. The miniprepped DNA was then subjected to SspI digestion and was found to be resistant to SspI. pSspIM14.0-B6 was also digested with EcoRV in 10 mM Tris-HCl, pH 7.9, 10 mM MgCl$_2$, 50 mM NaCl, 1 mM DTT, then a 13 Kb digestion product was gel prepped, religated and plated on 100 ug/ml ampicillin. The miniprepped DNA was subjected to SspI digestion and was found to be resistant to SspI. pSspIM14.0-B6 was also digested with XhoI in 10 mM Tris-HCl, pH 7.9, 10 mM MgCl$_2$, 50 mM NaCl, 1 mM DTT, then a 6.8 Kb digestion product was gel prepped, religated and plated on 100 ug/ml ampicillin. The miniprepped DNA was subjected to SspI digestion and was found to be resistant to SspI. pSspIM14.0-B6 was also double digested with ClaI and BstBI. The ClaI digest was carried out first in 20 mM Tris-acetate, pH 7.9, 10 mM magnesium acetate, 50 mM potassium acetate and 1 mM DTT at 37° C. Then 5,000 units of BstBI was added and the mixture was incubated at 65° C. for one hour. An 11. 4 kb digestion product was gel prepped, religated, and plated on 100 ug/ml ampicillin. The miniprepped DNA was subjected to SspI digestion and was found to be not resistant to SspI. The deletion clones of SspI methylase are summarized in FIG. 2.

From all these deletion clones, the smallest methylase containing region of DNA was between the BglII site and the XhoI site. Thus, 5 ug of pSspIM14.0-B6 were digested with 40 units of BglII and 40 units of XhoI in 50 mM Tris-HCl, pH 7.9, 10 mM MgCl$_2$, 100 mM NaCl, 1 mM DTT for 1 hour. The digestion products were run out on a 0.7% low melt agarose gel. The 1.2 Kb BglII-XhoI fragment was excised from the gel. The DNA was recovered from the gel using β-agarase as follows: the gel slice was melted at 55° C. and brought to 10 mM Tris-HCl (pH 6.5), 1 mM EDTA. Six units of β-agarase were added and the agarose was digested at 42° C. for 1 hour. The undigested carbohydrates were pelleted by spinning at 15,000× g at 4° C. for 15 minutes. The DNA containing supernate was brought to 0.5M NaCl and two volumes of isopropanol were added. This was mixed and chilled at −20° C. for 15 minutes before being centrifuged at 15,000× g for 15 minutes. The DNA pellet was washed in 70% isopropanol and dried. The DNA was resuspended in 20 ul of TE. 10 ul of the BglII-XhoI methylase fragment was ligated into the SalI- BamHI site of pUC18 and pUC19, respectively. These two methylase subclones were subjected to DNA sequencing. The DNA sequence obtained is shown in FIG. 3.

D. Preparation of SspI Endonuclease Protein, Protein Sequencing the SspI Endonuclease, and Mapping the Location of the SspI Endonuclease.

DC-1. SspI endonuclease from Sphaerotilus species designated NEB#315 was propagated in a fermenter at 37° C. in TRY-YE Broth medium consisting of: tryptone, 10.0 g per liter; yeast extract, 5.0 g per liter; NaCl, 2.0 g per liter; K$_2$HPO$_4$, 4.4 g per liter; glucose, 2.0 g per liter; hemin bovine, 10 mg per liter; NAD;DPN, 2.0 mg per liter. The cells are collected by centrifugation and the cell paste is used fresh or stored at −70° C. All subsequent steps are carried out at 4° C.

DC-2. The cell paste (253 grams) is thawed and the cells are resuspended in 500 ml sonication buffer (20 mM Tris-HCl, pH 7.6, 0.1 mM EDTA, 50 mM NaCl, 1 mM DTT).

D-3. The cells are disrupted by a gaulin mill to achieve release of approximately 35 mg of soluble protein per ml of suspended cells.

D-4. The insoluble cell debris is removed by centrifugation at 15,000× g for 40 minutes.

D-5. 50 g of Cell Debris Remover (Whatman) was added to the supernatant and centrifuged at 10,000× g for 10 minutes.

D-6. The supernatant fluid is applied to a phosphocellulose column (5×35 cm) (Whatman P-11) equilibrated with 20 mM K$_2$HPO$_4$, pH 6.9, 50 mM NaCl,0.1 mM EDTA, 1 mM DTT. The column is washed with two column volumes of the above buffer. The flow-though from the column is collected in a single flask. SspI endonuclease is retained by the column and elutes between 0.3 and 0.6M NaCl. The most active fractions are pooled and dialyzed overnight against 20 mM K$_2$HPO$_4$, pH7.4, 50 mM NaCl, 0.1 mM EDTA, 1 mM DTT.

D-7. The pool from the phosphocellulose column is applied to a Heparin-Sepharose CL-6B column (2.5×25 cm) equilibrated with 20 mM K$_2$HPO$_4$, pH 7.4, 0.05 mM NaCl, 0.1 mM EDTA, 1 mM DTT, and washed with two column volumes of the same buffer. A linear gradient of NaCl from 0.05M to 0.8M (total volume 500 ml) is developed and applied to the column. Three ml fractions are collected. The fractions are assayed for the presence of the SspI restriction endonuclease activity on lambda DNA. The active fractions are pooled and dialysed against 100 volumes of 20 mM K$_2$HPO$_4$, pH 7.4, 0.05 mM NaCl, 0.1 mM EDTA, 1 mM DTT.

D-8. The dialyzed pool (25 ml) of SspI activity is applied to a 1 ml Mono S FPLC column (Pharmacia) and washed with 20 mM K$_2$HPO$_4$, pH 7.4, 0.05 mM NaCl, 0.1 mM EDTA, 1 mM DTT and a 40 ml linear gradient from 50 mM KCl to 1.0M KCl is developed in the same buffer and applied to the column. One ml fractions are collected and assayed for the presence of SspI restriction endonuclease activity. The four most active fractions were homogeneous and were found to have a specific activity of approximately 140,000 units/mg protein and a molecular weight on SDS-polyacrylamide gels of 32,000 Daltons.

D-9. 4 ug of the homogeneous SspI endonuclease was subjected to amino terminal protein sequencing on an Applied Biosystems Model 470A gas phase protein sequencer (Brooks, et al., Nucleic Acids Research, 17:979–997, (1989)). The first 30 residues were degraded. The sequence of the first 25 residues obtained was the following: SKAAYQDFTKXSLLIKKXXNLITM (SEQ ID NO:1) (refer to Table 1 for explanation of 1 letter code for protein sequence ).

D-10. Based on the protein sequence, two 17-mers were made with the following sequences: 5'GCNGCNTAYC ARGACTT3' (SEQ ID NO:2) and 5'GCNGCNTAYCAR-GATTT3' (SEQ ID NO:3) (Y=T or C; D=A, G or T; R=A or G; N=A, C, G, or T) which were used to map the location of the amino terminal end of the endonuclease on Sphaerotilus genomic DNA.

The oligomer probes were end labelled with γ-32-P in the following manner: 5 ul of the oligomer probe (250 ng) is resuspended in 20 ul of 70 mM Tris-HCl, pH7.6, 10 mM MgCl$_2$, 5 mM DTT. 5 ul of γ-32-P is added followed by the addition of 1 ul T$_4$ Polynucleotide kinase. This was incubated at 37° C. for 30 minutes.

The Southern blot was prepared as follows: 1 ug of Sphaerotilus genomic DNA was digested with AseI, BamHI, BglII, BsmI, BstBI, BstEII, EcoRI, EcoRV, PstI, PvuII, SacII, SphI, or XhoI. The digests were run on a 0.7% agarose gel overnight. The gel was washed in two changes of 0.25M HCl for 15 minutes, then in two changes of 0.5M NaOH, 1.5 M NaCl for 15 minutes each and finally in two changes of 1M NH$_4$OAc, 0.02M NaOH for 30 minutes. To transfer the DNA to nitrocellulose, a sheet of 0.45 um pore size nitrocellulose was wet in 1M NH$_4$OAc, 0.02M NaOH and a piece the same size as the gel was placed on either side of the gel. This was placed on top of a two inch high stack of paper towels and another two inch stack of paper towels was placed on top. A glass plate was placed on the top of the stack and a small weight was placed on top. The DNA transfer was allowed to proceed overnight. The nitrocellulose was baked at 80° C. for one hour.

The nitrocellulose blot was pre hybridized in 15 mls of 50× Denhardt's (5 g ficoll, 5 g polyvinylpyrrolidone, 5 g BSA in 500 mls H$_2$O), 20× SSC (175.3 g NaCl, 88.2 g Sodium citrate in 1L H$_2$O), 10% SDS and 10% dextran sulfate. After prehybridizing at room temperature for one hour, the labelled probe was added and the hybridization step was carried out at 37° C. overnight. The blot was washed in three changes of 2× SSC and three changes of 2× SSC with 0.1% SDS over the period of one hour at 37° C. The blot was exposed to X-ray film for 4 and 7 days.

From this blot, and the map of the pSspIM14.0-B 6 clone, a genomic map in the region of the restriction endonuclease was constructed. FIG. 5 is a map of the restriction sites in the region of the SspI restriction/modification system in the Sphaerotilus genome.

II. Cloning the SspI Restriction System.

A. Preparation of new libraries in an McrA[31] host.

A-1. Based on the DNA sequence of the methylase, PCR primers were designed. The primer for the N-terminal is as follows 5'GCTTGAAGATCTAGAGGATTTCATA TGG-GATCAATGTTTAACACCACACAA3' (SEQ ID NO: 4) The sequence of the C-terminal primer is: 5'TTCTTGTTG-GCGTTCGCTCGAGC ACCCAGTTAGGAA3' (SEQ ID NO:5). The SspI methylase was amplified out of pSspIM14.0-B6 as follows: 2 ng of template DNA was diluted in 10 mM KCl, 20 mM Tris-HCl (pH 8.8), 10 mM (NH$_4$)$_2$SO$_4$, 6 mM MgSO$_4$, 0.1% Triton X-100; 200 uM dNTP's, the primers, and 1 U of Vent DNA polymerase was added. Thirty five cycles of denature at 95° C. for 1 minute, anneal at 72° C. for 1 minute and extend at 75° C. for 2 minutes were run in a thermal cycler. A 1.1 Kb PCR product was obtained. The PCR product was microdialyzed against TE for one hour, then 10 ul was digested with BglII and XhoI as follows: 10 ul of PCR product plus 2 ul of 500 mM Tris-HCl, pH 7.9, 100 mM MgCl$_2$, 1M NaCl, 10 mM DTT, plus 4 ul H$_2$0, plus 24 units of BglII and 20 units of XhoI were incubated at 37° C. overnight.

The vector was prepared as follows: 5 ug of pUC18 or pUC19 was incubated in 20 ul of 150 mM NaCl, 10 mM Tris-HCl, pH 7.9, 10 mM MgCl$_2$, 1 mM DTT; 20 units of BamHI and 60 units of SalI were added. The digests were incubated for 1 hour at 37° C. The DNA was then phenol/chloroform extracted and ethanol precipitated. The DNA was resuspended in 50 ul TE.

The plasmids and BglII-XhoI cut PCR product were ligated overnight at 16° C. The amplified methylase constructs were transformed into E. coli strain ER2252 and competent cells were prepared. The methylase in pUC19 (running in the opposite orientation of the lac promotor) is construct pSspM-A8. The methylase in pUC18 (running in the same orientation as the lac promotor) is construct pSspM-B5.

A-2. Based on the data obtained in I (D-10), purified Sphaerotilus species genomic DNA (prepared as in I (A-1)) was subjected to a limit digestion using SphI, or XhoI as follows: 10 ug of genomic DNA was diluted into 10 mM Tris-HCl, pH 7.9, 10 mM MgCl$_2$, 50 mM NaCl, 1 mM DTT, 50 units of SphI or XhoI were added to the appropriate tube. The tubes were incubated at 37° C. for one hour, then phenol/chloroform extracted and ethanol precipitated. The pellets were redissolved in 50 ul of 10 mM Tris-HCl, 1 mM EDTA, pH 8.0 and 1 ul from each analyzed by agarose gel electrophoresis.

The pACYC184 vectors were prepared as follows: 10 ug of pACYC184 was resuspended in 200 ul of 10 mM Tris-HCl, o pH 7.9, 10 mM MgCl$_2$, 50 mM NaCl, 1 mM DTT. 40 units of SphI or SalI was added and the digest was incubated at 37° C. for one and a half hours at which time 4 units of cip were added and the incubation continued for another 30 minutes. The digests were phenol/chloroform extracted and ethanol precipitated. The pellets were resuspended in 100 ul of TE.

Ligation was as follows: 10 ug of SphI cut genomic DNA was mixed with 10 ug of SphI cut pACYC184 in 50 ul of ligation buffer (50 mM Tris, pH 7.5, 10 mM MgCl$_2$ 10 mM DTT, 0.5 mM ATP), 1 ul of T$_4$ DNA ligase was added and the mixture incubated at 16° C. overnight. 10 ug of the XhoI cut genomic DNA was mixed with 10 ug of SalI cut and dephosphorylated pACYC184 in 50 ul of ligation buffer. 1 ul of T$_4$ DNA ligase was added and the mixture incubated at 16° C. overnight.

A-3. A primary cell library was prepared as in step I A-4 except that it was transformed into ER2252 cells pre-protected with pSspM-A8 or pSspM-B5. The DNA from the primary cell library was digested with the following restriction enzymes, AseI, BamHI, BglII, BsmI, BstBI, BstEII, EcoRI, EcoRV, PstI, PvuII, SacII, SphI, or XhoI; run on a 0.7% agarose gel overnight, and the gel prepared for Southern blotting as in I (B-3). The Southern blots were probed with the two degenerate oligos for the N-terminal of Ssp endonuclease used as in I (D-10). No endonuclease containing clone was identified from the Southern blot.

B. Inverted PCR of Sphaerotilus species genomic DNA.

B-1. The template Spaerotilus species DNA for PCR was prepared as in I (A-1). The DNA was then digested with SacII as follows: 5 ug of genomic DNA was resuspended in 95 ul of 20 mM Tris-acetate, 10 mM magnesium acetate, 50 mM potassium acetate, 1 mM DTT, 5 ul (100 units) of SacII was added and the mixture was incubated at 37° C. for 1 hour. The digest was phenol/chloroform extracted, and ethanol precipitated. The DNA pellet was resuspended in 500 ul of 1× ligase buffer (50 mM Tris-HCl, pH 7.8, 10 mM MgCl$_2$, 10 mM DTT, 1 mMATP, 25 ug/ml BSA), then 1 ul of T$_4$ DNA ligase was added. The ligation was allowed to proceed at 16° C. overnight. The ligase was heat killed for 15 minutes at 65° C.

B-2. The primers used for inverse PCR were derived from DNA sequence within the methylase gene. The sequence of the clockwise 30-mer is as follows: TGAGTGGC TTAGG-GATGCAGAAGAGCCAAA (SEQ ID NO:6). The sequence of the counterclockwise primer is: TTGGTCACT-TCATTTCGCCATGA CATTTCG (SEQ ID NO:7).

1 ug of SacII cut and religated genomic template (as prepared in II B-1) was mixed with 10 mMKCl, 20 mMTris-HCl (pH 8.8), 10 mM $(NH_4)_2SO_4$, 2 mM $MgSO_4$, 0.1% Triton X-100; 200 uM dNTP's, the primers, and 1 U of Vent DNA polymerase was added. Thirty cycles of denature at 95° C. for 1 minute, anneal at 65° C. for 1 minute, and extend at 72° C. for 4 minutes were run in a thermal cycler. A 4 kb PCR product was observed.

B-3. The 4 kb PCR product was run on a 0.7% low melt agarose gel. The PCR product was excised from the gel and random primed using the NEBlot kit as follows. The gel slice was melted at 65° C. and it's volume determined to be 70 ul. 10 ul of 10× random priming buffer was added and 250 uMoles of dATP, dTTP and dGTP were added. 1 ul of DNA-Polymerase I-Klenow fragment and 5 ul of $^{32}P$-γ-dCTP were added. The random priming reaction was allowed to continue for 6 hours at 37° C. The random primed PCR product was used to probe a Southern blot of Ssp genomic DNA digested with AseI, BamHI, BglII, BsmI, BspHI, BstBI, BstEII, EcoRV, NcoI, NdeI, PstI, PvuII, SacII, SphI, and XhoI. Hybridization was carried out overnight at 68° C. The blot was washed 5 times with 2× SSC. The blot was exposed to X-ray film for 4 hours, then developed. It was determined that the inverse PCR product mapped to the location of the SspI endonuclease.

B-4. The inverse PCR product was cloned into pACYC184 in the following manner. First, the vector was cut with EcoRV and dephosphorylated. 8 ug of pACYC184 was resuspended in 100 ul of 10 mM Tris-HCl, pH 7.9, 10 mM $MgCl_2$, 50 mM NaCl, 1 mM DTT; 6 units of EcoRV were added and the digest was incubated at 37° C. for one and a half hours. 10 units of calf intestinal phosphatase were added and the reaction allowed to proceed for another 30 minutes. The DNA was phenol/chloroform extracted and ethanol precipitated. The SspI endonuclease from inverse PCR was kinased in 100 ul of 70 mM Tris-HCl, pH 7.6, 10 mM $MgCl_2$, 5 mM DTT, and 66 uM dATP with 10 units of $T_4$ polynucleotide kinase. The kinased inverse PCR product was then ligated into the EcoRV cut and dephsphorylated pACYC184 as follows: 1 ug of EcoRV cut and dephosphorylated pACYC184 was resuspended in 1× ligase buffer (50 mM Tris-HCl, pH 7.8, 10 mM $MgCl_2$, 10 mM DTT, 1 mMATP, 25 ug/ml BSA). 20 ul of the kinased inverse PCR product was added along with 800 units of $T_4$ DNA ligase. The ligation reaction was allowed to proceed for 1 hour at room temperature, then 5 ul was transformed into pSspM-A8 and pSspM-B5 pre-protected ER 2252 cells (as prepared in II A-1).

The cells were scraped off the plate and DNA was prepared as for the primary cell libraries (Secton I A-4). The DNA was digested with the following enzymes: AseI, BamHI, BglII, EcoRI, EcoRV, NsiI, PstI, SacII, SalI, SphI, and XhoI; then run out on a 0.7% agarose gel and Southern blotted. The Southern blots were probed with a kinased 30-mer (kinased as in I D-10) specific for the C-terminal of the SspI endonuclease with the sequence: GCT-GTTTCAGCTCTGGCACGTGCGGCATCG (SEQ ID NO: 8 ). The DNA encoding the endonuclease gene was not detected.

B-5. The inverse PCR product was cut with XhoI and BglII to isolate the N-terminal half of the endonuclease gene. 10 ul of the inverse PCR product was microdialyzed against TE for 1 hour. The inverse PCR product was then brought to 50 mM Tris-HCl, pH 7.9, 10 mM $MgCl_2$, 100 mM NaCl, 1 mM DTT; 8 units of BglII and 20 units of XhoI were added. This was allowed to incubate at 37° C. for one hour. The restriction enzymes were heat killed by incubating for 20 minutes at 65° C. This was ligated to pUC19 which had been cut with BamHI and SalI. 100 ng of BamHI and SalI cut pUC19 was resuspended in ligase buffer. 20 ul of the BglII-XhoI cut inverse PCR product was added and 400 units of $T_4$ DNA ligase were added. The ligation was allowed to proceed overnight at 16° C. 20 ul of the ligation was transformed into ER 2267 and plated on 50 ug/ml ampicillin with 80 ng X-gal and 10 mM IPTG.

Several white colonies were picked and grown in a 10 ml overnight culture. These cells were then miniprepped and 50% were determined to have an insert.

B-6. The minipreps determined to have insert DNA (from II B-5) were mapped with BamHI, SalI, EcoRI and SacII to determine if the insert had the correct restriction map to be the N-terminal half of the SspI endonuclease. The BamHI and SalI digests were done on 1 ug of miniprep DNA resuspended in 150 mM NaCl, 10 mM Tris-HCl (pH 7.9), 10 mM $MgCl_2$, and 1 mM DTT with 20 units of BamHI or 20 units of SalI. The EcoRI digests were done with 20 units of EcoRI in 50 mM NaCl, 100 mM Tris-HCl (pH 7.5), 10 mM $MgCl_2$, and 0.025% triton X-100. The SacII digests were done with 20 units of SacII in 50 mM potassium acetate, 20 mM Tris-acetate (pH 7.9), 10 mM magnesium acetate, and 1 mM DTT. One ug of miniprep DNA was digested in each of the above reactions for 1.5 hours at 37° C. Half of the insert DNA mapped had the correct structure to be the N-terminal half of the SspI endonuclease.

C. Using PCR to amplify the restriction endonuclease gene.

C-1. Two oligonucleotide primers were designed for amplifying the SspI endonuclease gene directly out of genomic DNA. The primer for the N-terminal of the gene was based on the degenerate amino acid sequence obtained in I-D-9 with an NdeI and XbaI site engineered in. The sequence of the N-terminal oligo is: GCTCTAGAC-CCGGGCATATG TCVAAAGCMGCMTAYCAAGATTT-TAA (SEQ ID NO:9) (where V=A, C, or G; M=A or C; Y=C. or T) The oligo for the C-terminal was: CAATTT-TAGTTTGGATCCGGCATATTT GGTACCTTGAGTTTC-CGGAG (SEQ ID NO:10).

C-2. Sphaerotilus species genomic template DNA for PCR was prepared as in I A-1. 1 ug of genomic template DNA was resuspended in 10 mM KCl, 20 mM Tris-HCl (pH 8.8), 10 mM $(NH_4)_2SO_4$, 6 mM $MgSO_4$, 0.1% Triton X-100, 200 uM dNTP's and 1 unit of Vent DNA polymerase. Thirty cycles of the following steps were performed in a thermal cycler: denature at 95° C. for 1 minute, anneal at 55° C. for 1 minute and extend at 73° C. for 2 minutes. A 900 base pair PCR product, believed to be the entire SspI endonuclease gene, was identified as the major product.

The 900 bp PCR product was microdialyzed against TE for 1 hour, then characterized by mapping with EcoRI, BglII, and BamHI. The PCR product was then digested with NdeI and BamHI as follows: 70 ul of the PCR product was brought to 150 mM NaCl, 10 mM Tris-HCl (pH 7.9), 10 mM $MgCl_2$, 1 mM DTT; 40 units of BamHI and 40 units of NdeI were added. The digest was incubated at 37° C. for one hour then run on a 1% low melt agarose gel. The band was excised and the DNA was recovered from the gel using β-agarase as follows: the gel slice was melted at 55° C. and brought to 10 mM Tris-HCl (pH 6.5), 1 mM EDTA. Six units of β-agarase were added and the agarose was digested at 42° C. for 1 hour. The undigested carbohydrates were pelleted by spinning at 15,000× g at 4° C. for 15 minutes. The DNA containing supernate was brought to 0.5M NaCl and two volumes of isopropanol were added. This was mixed and chilled at −20° C. for 15 minutes before being centrifuged at 15,000× g for 15 minutes. The DNA pellet was washed in 70% isopropanol and dried. The DNA was resuspended in 20 ul of TE.

D. Cloning the PCR product into the vector pAII17.

D-1. 5 ug of the vector pAII17 (a $T_7$ expression vector derived from pET 11c; Kong, et.al *J. Biol. Chem.* 268:1965-1975 (1993)) was resuspended in 50 mM Tris-HCl, pH 7.9, 10 mM $MgCl_2$, 100 mM NaCl, 1 mM DTT. 60 units of NdeI and 80 units of BamHI were added and the mixture incubated at 37° C. for one hour. The digest was run out on a 0.7% low melt agarose gel and the 6.2 Kb band was excised from the gel. The band from the gel was melted and the DNA recovered with βagarase as in II C-2. The DNA pellet was resuspended in 20 ul of $H_2O$.

The PCR product obtained in II C-2 was ligated into the NdeI-BamHI cut pAII17 as follows: 1 ug of the PCR product cut with BamHI and NdeI and 1 ug of pAII17 cut with NdeI-BamHI were resuspended in 50 mM Tris-HCl, pH 7.8, 10 mM $MgCl_2$, 10 mM DTT, 1 mMATP, 25 ug/ml BSA and 400 units of $T_4$ DNA polymerase was added. The ligation was allowed to proceed at 16° C. overnight.

2 ul of the ligation was transformed into RR1 with no pre-protecting SspI methylase and 2 ul was transformed into ER 2169, also lacking the cognate methylase, and plated on 50 ug/ml ampicillin. After 18 hours, 96 colonies were picked off each plate and replicated on master plates containing 50 ug/ml ampicillin. The ER 2169 transformants were also replicated on a plate with 1 mM IPTG and ampicillin. After 18 hours, it was noted that several colonies from ER 2169 grown on the IPTG had lysed.

DC-2. Ten ml overnight cultures were grown of the first 18 colonies from the ER 2169 plate. When it was noted which colonies had lysed in the presence of IPTG, 1 ml of the corresponding 10 ml culture was diluted out 10-fold and induced with 10 mM IPTG at mid-log phase. The cell cultures were grown for 3 hours in the presence of IPTG. 1.5 mls of the culture was spun down in a microfuge tube. The cell pellets were resuspended in 400 ul of 20 mM $KH_2PO_4$, 50 mM NaCl, 1 mM DTT. The cells were sonicated for 10 seconds to break the cells. The cell debris was spun down for 5 minutes at 15,000× g. The supernatant was assayed for SspI activity on lambda DNA.

The assay for SspI activity proceeded as follows: 1 ug of lambda DNA was diluted to 10 mM Tris-HCl, 10 mM $MgCl_2$, 50 mM NaCl, 1 mM DTT in a total volume of 20 ul. 1 ul of the supernatant from the sonicated cells was added and incubated for 30 minutes at 37° C. The digest was run on a 0.7% agarose gel. SspI activity was detected in 6 out of 7 of the crude cell extracts. FIG. 8 is a photograph of an agarose gel demonstrating SspI restriction endonuclease activity. The plasmids with SspI activity were grown and CsCl prepped and are referred to as p (pAII17) SspR7.2-A3, p (pAII17) SspR7.2-A9, p (pAII17)-SspR7.2-A10, p (pAII17) SspR7.2-A12, p (pAII17) SspR7.2-B1, and p (pAII17) SspR7.2-B6.

Plasmid p (pAII17) SspR7.2-B1 was deposited with the American Type Culture Collection (ATCC) under the terms of the Budapest Treaty on Oct. 6, 1994, and received ATCC Accession No 7590.9.

What is claimed is:

1. Isolated DNA coding for the SspI restriction endonuclease, wherein the isolated DNA is obtainable from the vector p (pAII17) SspR7.2-B1.

2. A recombinant DNA vector comprising a vector into which a DNA segment coding for the SspI restriction endonuclease has been inserted.

3. Isolated DNA coding for the SspI restriction endonuclease and methylase, wherein the isolated DNA is obtainable from the vector p(pAII17)SspR7.2-B1.

4. A cloning vector which comprises the isolated DNA of claim 3.

5. The cloning vector of claim 4, wherein the vector comprises p(pAII17)SspR7.2-B1.

6. A host cell transformed by the cloning vector of claim 2, 4 or 5.

7. A method of producing an SspI restriction endonuclease comprising culturing a host cell transformed with the vector of claim 2, 4 or 5 under conditions suitable for expression of said endonuclease.

* * * * *

UNITED STATES PATENT AND TRADEMARK OFFICE
CERTIFICATE OF CORRECTION

PATENT NO. : 5,516,678                                  Page 1 of 3
DATED      : May 14, 1996
INVENTOR(S): Benner, et al.

It is certified that error appears in the above-indentified patent and that said Letters Patent is hereby corrected as shown below:

Title page, Item [54] replace "SSPI" with --*Ssp*I--

Column 1, line 1, replace "SSPI" with --*Ssp*I--

Column 3, line 26, replace "Mrr-" with --Mrr⁻--

Column 4, line 26, after "pAII17" insert --Lane 1 lambda *Bst*EII digest marker; Lane 2 supernatant (no substrate) of p(pAII17)SsspR7.2-A3; Lane 3 supernatant of p(pAII17)SspR7.2-A3 incubated with lambda DNA; Lane 4 supernatant (no substrate) of p(pAII17)SspR7.2-A9; Lane 5 supernatant of p(pAII17)SspR7.2-A9 incubated with lambda DNA; Lane 6 supernatant (no substrate) of p(pAII17)SspR7.2-A10; Lane 7 supernatant of p(pAII17)SspR7.2-A10 incubated with lambda DNA; Lane 8 supernatant (no substrate) of p(pAII17)SspR7.2-A12; Lane 9 supernatant of p(pAII17)SspR7.2-A12 incubated with lambda DNA; Lane 10 supernatant of p(pAII17)SspR7.2-B1 incubated with lambda DNA; Lane 12 supernatant (no substrate) of p(pAII17)SspR7.2-B3; Lane 13 supernatant of p(pAII17)SspR7.2-B3 incubated with lambda DNA; NOTE: this isolate shows no *Ssp*I activity; Lane 14 supernatant (no substrate) of p(pAII17)SspR7.2-B6; Lane 15 supernatant of p(pAII17)SspR7.2-B6 incubated with lambda DNA; Lane 16 lambda DNA incubated with SspI; Lane 17 lambda DNA BstEII digest marker--

UNITED STATES PATENT AND TRADEMARK OFFICE
CERTIFICATE OF CORRECTION

PATENT NO. : 5,516,678
DATED : May 14, 1996
INVENTOR(S) : Benner, et al.

It is certified that error appears in the above-indentified patent and that said Letters Patent is hereby corrected as shown below:

Column 5, line 28, replace "C Mapping" with
--C. Mapping--

Column 5, line 42, replace "b 6" with --B6--

Column 5, line 51, replace "DC-1" with --D-1--

Column 5, line 66, replace "DC-3" with --D-3--

Column 6, line 4, replace "DC-4" with --D-4--

Column 6, line 22, replace "pre-protected overexpressed"
with --pre-protected with the overexpressed--

Column 7, line 6, replace "DC-1" with --D-1--

Column 7, line 8, replace "pET 11c" with --pET11c--

Column 7, line 9, replace "19 75" with --1975--

Column 7, line 13, replace "DC-2" with --D-2--

Column 12, line 1, replace "DC-1" with --D-1--

Column 12, line 10, replace "DC-2" with --D-2--

Column 12, line 62, replace "Table 1" with --Figure 11--

Column 13, replace "McrA$^{31}$" with --McrA$^-$--

Column 14, line 25, replace "HC-1, o pH" with --HC-1, pH--

UNITED STATES PATENT AND TRADEMARK OFFICE
CERTIFICATE OF CORRECTION

PATENT NO. : 5,516,678
DATED : May 14, 1996
INVENTOR(S) : Benner, et al.

It is certified that error appears in the above-indentified patent and that said Letters Patent is hereby corrected as shown below:

Sheet 1 of 16, line 2, replace "Bgl II" with --BglII--

Sheet 1 of 16, line 6, replace "CsCl" with --CsCl--

Column 4, line 29, replace "N: 17" with --NO:17--

Column 12, line 23, replace "NaCl,0.1" with --NaCl, 0.1--

Column 13, line 27, replace "pre hybridized" with --pre-hybridized--

Column 15, line 43, replace "dephsphorylated" with --dephosphorylated--

Column 17, replace "ßagarase" with --ß-agarase--

Column 18, replace "DC-2" with --D-2--

Column 18, line 32, replace "7590.9." with --75909.--

Signed and Sealed this

Tenth Day of September, 1996

Attest:

BRUCE LEHMAN

*Attesting Officer*      *Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO: 1:

( i ) SEQUENCE CHARACTERISTICS:
        ( A ) LENGTH: 24 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 11
        ( D ) OTHER INFORMATION: /note="X at Position 11 = Any amino acid"

( i x ) FEATURE:
        ( A ) NAME/KEY: Protein
        ( B ) LOCATION: 18
        ( D ) OTHER INFORMATION: /note="; X at Position 18 = Serine or Histidine"

( i x ) FEATURE:
        ( A ) NAME/KEY: Protein
        ( B ) LOCATION: 19
        ( D ) OTHER INFORMATION: /note="X at Position 19 = Any amino acid"

( x i ) SEQUENCE DESCRIPTION: SEQ ID NO: 1:

Ser Lys Ala Ala Tyr Gln Asp Phe Thr Lys Xaa Ser Leu Leu Ile
             5                         10                      15

```
        Lys  Lys  Xaa  Xaa  Asn  Leu  Ile  Thr  Met
                        20
```

( 2 ) INFORMATION FOR SEQ ID NO: 2:

( i ) SEQUENCE CHARACTERISTICS:
    ( A ) LENGTH: 17 base pairs
    ( B ) TYPE: nucleic acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO: 2:

GCNGCNTAYC ARGACTT                    17

( 2 ) INFORMATION FOR SEQ ID NO: 3:

( i ) SEQUENCE CHARACTERISTICS:
    ( A ) LENGTH: 17 base pairs
    ( B ) TYPE: nucleic acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO: 3:

GCNGCNTAYC ARGATTT                    17

( 2 ) INFORMATION FOR SEQ ID NO: 4:

( i ) SEQUENCE CHARACTERISTICS:
    ( A ) LENGTH: 51 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO: 4:

GCTTGAAGAT CTAGAGGATT TCATATGGGA TCAATGTTTA ACACCACACA A          51

( 2 ) INFORMATION FOR SEQ ID NO: 5:

( i ) SEQUENCE CHARACTERISTICS:
    ( A ) LENGTH: 36 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO: 5:

TTCTTGTTGG CGTTCGCTCG AGCACCCAGT TAGGAA          36

( 2 ) INFORMATION FOR SEQ ID NO: 6:

( i ) SEQUENCE CHARACTERISTICS:
    ( A ) LENGTH: 30 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO: 6:

TGAGTGGCTT AGGGATGCAG AAGAGCCAAA          30

5,516,678

21

-continued ( 2 ) INFORMATION FOR SEQ ID NO: 7:

( i ) SEQUENCE CHARACTERISTICS:
    ( A ) LENGTH: 30 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO: 7:

TTGGTCACTT CATTTCGCCA TGACATTTCG                   30

( 2 ) INFORMATION FOR SEQ ID NO: 8:

( i ) SEQUENCE CHARACTERISTICS:
    ( A ) LENGTH: 30 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO: 8:

GCTGTTTCAG CTCTGGCACG TGCGGCATCG                   30

( 2 ) INFORMATION FOR SEQ ID NO: 9:

( i ) SEQUENCE CHARACTERISTICS:
    ( A ) LENGTH: 46 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO: 9:

GCTCTAGACC CGGGCATATG TCVAAAGCMG CMTAYCAAGA TTTTAA         46

( 2 ) INFORMATION FOR SEQ ID NO: 10:

( i ) SEQUENCE CHARACTERISTICS:
    ( A ) LENGTH: 47 base pairs
    ( B ) TYPE: nucleic acid
    ( C ) STRANDEDNESS: unknown
    ( D ) TOPOLOGY: unknown ( i i ) MOLECULE TYPE: DNA (genomic)

( x i ) SEQUENCE DESCRIPTION: SEQ ID NO: 10:

CAATTTTAGT TTGGATCCGG CATATTTGGT ACCTTGAGTT TCCGGAG        47

( 2 ) INFORMATION FOR SEQ ID NO: 11:

( i ) SEQUENCE CHARACTERISTICS:
    ( A ) LENGTH: 2061 base pairs
    ( B ) TYPE: nucleic acid
    ( C ) STRANDEDNESS: unknown
    ( D ) TOPOLOGY: unknown ( i i ) MOLECULE TYPE: DNA (genomic)

( i x ) FEATURE:
    ( A ) NAME/KEY: CDS
    ( B ) LOCATION: 2..640
    ( D ) OTHER INFORMATION: /note="This indicates the
      C-terminal portion of the endonuclease"

( x i ) SEQUENCE DESCRIPTION: SEQ ID NO: 11:

G GAT CTC TAT CGC GCA AAG TCA AAG GAA GAA GAT ATC ACG GTT GAG    46
 Asp Leu Tyr Arg Ala Lys Ser Lys Glu Glu Asp Ile Thr Val Glu

```
  1                        5                              10                             15
AAC  GAA  ATC  ACA  AAG  GAA  AAA  TTC  CCC  ATC  AGC  CTC  AAG  GCT  TAT  GGG          94
Asn  Glu  Ile  Thr  Lys  Glu  Lys  Phe  Pro  Ile  Ser  Leu  Lys  Ala  Tyr  Gly
               20                        25                       30

GAT  GGT  CCA  CTA  CAG  CTT  TCA  ACT  GAC  AAA  AAT  TTT  TTG  ATG  TAC  CCT         142
Asp  Gly  Pro  Leu  Gln  Leu  Ser  Thr  Asp  Lys  Asn  Phe  Leu  Met  Tyr  Pro
               35                        40                       45

CTT  CTT  GAG  GAA  ATT  GGG  GCG  TTC  ATC  AAT  GCC  AAA  GAA  AAA  ATA  GAA         190
Leu  Leu  Glu  Glu  Ile  Gly  Ala  Phe  Ile  Asn  Ala  Lys  Glu  Lys  Ile  Glu
               50                        55                       60

GAA  ATT  TTT  GCC  AAT  GAA  GCA  TTT  TCG  TGC  TTC  AGC  GAA  ATA  AAT  GTC         238
Glu  Ile  Phe  Ala  Asn  Glu  Ala  Phe  Ser  Cys  Phe  Ser  Glu  Ile  Asn  Val
          65                        70                       75

CTA  CCC  TTG  ATA  TAC  GAT  GAG  AAG  AGG  CAG  CGA  TGT  AAT  ATT  TTG  GTT         286
Leu  Pro  Leu  Ile  Tyr  Asp  Glu  Lys  Arg  Gln  Arg  Cys  Asn  Ile  Leu  Val
80                        85                       90                       95

TTC  GAT  GCC  GCA  CGT  GCC  AGA  GCT  GAA  ACA  GCT  TAC  ATT  CGC  AAA  GAA         334
Phe  Asp  Ala  Ala  Arg  Ala  Arg  Ala  Glu  Thr  Ala  Tyr  Ile  Arg  Lys  Glu
                    100                       105                      110

ACA  GAG  GGG  TCA  GGA  CGA  AAA  CAC  CCG  GCT  TAC  AGA  TTT  TTT  GAC  AAA         382
Thr  Glu  Gly  Ser  Gly  Arg  Lys  His  Pro  Ala  Tyr  Arg  Phe  Phe  Asp  Lys
               115                       120                      125

AAT  AAA  AAT  TAC  ATC  TGC  GAA  GTG  CGC  TAC  GGG  AAT  GCT  GCG  GCA  AAT         430
Asn  Lys  Asn  Tyr  Ile  Cys  Glu  Val  Arg  Tyr  Gly  Asn  Ala  Ala  Ala  Asn
          130                       135                      140

GCG  CTC  CAA  CGA  GGA  CTT  TGG  ACA  AAC  ACA  AAA  AAT  GCT  ACA  TCA  TTT         478
Ala  Leu  Gln  Arg  Gly  Leu  Trp  Thr  Asn  Thr  Lys  Asn  Ala  Thr  Ser  Phe
          145                       150                      155

TTT  GAT  AGT  GTA  ACA  AAC  GGC  TGG  GTT  GAT  TAC  TCT  CAT  AAC  TTG  GTC         526
Phe  Asp  Ser  Val  Thr  Asn  Gly  Trp  Val  Asp  Tyr  Ser  His  Asn  Leu  Val
160                       165                      170                      175

TTA  GTT  AAG  CTG  CTT  TCG  CAC  GCT  TTG  GTT  TCA  AGT  CGC  AAA  GGC  CAC         574
Leu  Val  Lys  Leu  Leu  Ser  His  Ala  Leu  Val  Ser  Ser  Arg  Lys  Gly  His
                    180                       185                      190

GAA  GCT  GCA  CTG  GAA  GAG  ATC  AAG  AAA  GAC  ATC  CTG  CAA  CTA  AAG  CAA         622
Glu  Ala  Ala  Leu  Glu  Glu  Ile  Lys  Lys  Asp  Ile  Leu  Gln  Leu  Lys  Gln
               195                       200                      205

ACG  AAT  GGG  ATC  AAT  GTT  TAACACCACA  CAACCATTGT  TTGAAAAGT                        670
Thr  Asn  Gly  Ile  Asn  Val
               210

AATTTTAGAC  ACTCCGGAAA  CTCAAGGAAT  AAAATATGCC  GGATCAAAAC  TAAAATTGAT                 730

CCAACACATT  TTATCCCTAC  TTGACAACCT  AGATGTAAAA  ACCGTATTCG  ATGGATTTTC                 790

TGGAACTACT  AGGGTCTCGC  AGGCCTTGGC  GAAGTGCGGA  TTTCATGTCA  CCAGCAACGA                 850

CATTTCAGAT  TGGTCTTATG  TATTTGGCTT  GTGCTACCTA  AAAAACAAAA  AACACCCCAA                 910

CGAATACAAG  GAACTAATTG  AACACCTTAA  CTCAATAAAT  GGCTACGACG  GTTGGTTCAC                 970

TGAGAAGTAT  GGCGGCCTTG  ACTATTCAGG  CAGTGCTATT  CAACCTGACG  GCACAAAAAA                1030

ACCTTGGCAA  GTCCACAATA  CGCGGAAGCT  AGATGGGATC  CGCGACGAAA  TAGATTCATT                1090

ATCACTGAAT  GAAACCGAAA  AAGCCGTCGC  CCTTACCAGT  TTAATTTTAG  CAATGGACGA                1150

AGTCGACAAC  ACACTTGGCC  ACTTCACTTC  ATACCTAAAA  GAATGGTCCC  CTCGATCATT                1210

CAAAGAAATG  CGAATGAAAA  TCCCAAAAAT  ATTTATTAAC  TCCGAAGACA  CCAAGTATT                 1270

AAAAGGCGAT  ATATTCGCAT  CAATGACTAA  CATCAATGTC  GATTTTGCTT  ACTTTGATCC                1330

ACCTTACGGT  TCAAACAACG  AAAAGATGCC  TCCTTCGCGA  GTACGCTATG  CATCGTATTA                1390

TCATTTATGG  ACAACTATAT  GCAAGAATGA  TAAGCCGAGC  ATTTTCGGAG  CCGCAGGCAG                1450
```

```
AAGATTAGAT ACATCAGATA AAATTGCAGC AACCGTTTTT GAAGAGTTTC GAAAAGATGA    1510

TGATGGTAAA TTTATTGCAG TTAAAGCAAT TGATAAATTA ATAAAAAACA TTCAAGCACG    1570

ATATGTTGCC CTTTCCTACA GTTCGGGCGG AAAAGCCACT GCCGAGGAGC TAGGCGAAAT    1630

ACTTAACCGC CACGGAAAAA TTATAAAAAC AATTGAAGTT GATCACAAGC GAAATGTCAT    1690

GGCAGAAATG AAGTGGACCA ATGAGTGGCT TAGGGATGCA GAAGAGCCAA ATCGAGAGTT    1750

TATTTTTCTC ATTGAAAAAA ATTCCTAACT GGGTGGTCAA GCGAACGCCA ACAAGGACCA    1810

CGGCTTCGCC GTTTTTACGG TCCCTGTTGG TGCCATTCAC TCGCTTCGCT CCTTCCGGAG    1870

CCGTGCTTGA CACGGCGATC GGCTTTGGCC TGGTGTCCGT GGCCGCCGTG GCGGCGGTGT    1930

TTGGAAAATT TCTGCTCGGC GGGTTGCTGG CCGCATTGGC GCTGGGCGTA TTTGTTCGTC    1990

TGAAGCGCCG CACGAAGTCC TGAGCGTCTG CACGGACGCG TTGTTCTCGA TGTCGAACTG    2050

CGGGGCTCGA C                                                          2061
```

( 2 ) INFORMATION FOR SEQ ID NO: 12:

( i ) SEQUENCE CHARACTERISTICS:
( A ) LENGTH: 213 amino acids
( B ) TYPE: amino acid
( D ) TOPOLOGY: linear ( i i ) MOLECULE TYPE: protein ( x i ) SEQUENCE DESCRIPTION: SEQ ID NO: 12:

```
Asp Leu Tyr Arg Ala Lys Ser Lys Glu Glu Asp Ile Thr Val Glu Asn
 1               5                  10                  15

Glu Ile Thr Lys Glu Lys Phe Pro Ile Ser Leu Lys Ala Tyr Gly Asp
             20                  25                  30

Gly Pro Leu Gln Leu Ser Thr Asp Lys Asn Phe Leu Met Tyr Pro Leu
         35                  40                  45

Leu Glu Glu Ile Gly Ala Phe Ile Asn Ala Lys Glu Lys Ile Glu Glu
     50                  55                  60

Ile Phe Ala Asn Glu Ala Phe Ser Cys Phe Ser Glu Ile Asn Val Leu
 65                  70                  75                  80

Pro Leu Ile Tyr Asp Glu Lys Arg Gln Arg Cys Asn Ile Leu Val Phe
                 85                  90                  95

Asp Ala Ala Arg Ala Arg Ala Glu Thr Ala Tyr Ile Arg Lys Glu Thr
            100                 105                 110

Glu Gly Ser Gly Arg Lys His Pro Ala Tyr Arg Phe Phe Asp Lys Asn
        115                 120                 125

Lys Asn Tyr Ile Cys Glu Val Arg Tyr Gly Asn Ala Ala Ala Asn Ala
130                 135                 140

Leu Gln Arg Gly Leu Trp Thr Asn Thr Lys Asn Ala Thr Ser Phe Phe
145                 150                 155                 160

Asp Ser Val Thr Asn Gly Trp Val Asp Tyr Ser His Asn Leu Val Leu
                165                 170                 175

Val Lys Leu Leu Ser His Ala Leu Val Ser Ser Arg Lys Gly His Glu
                180                 185                 190

Ala Ala Leu Glu Glu Ile Lys Lys Asp Ile Leu Gln Leu Lys Gln Thr
        195                 200                 205

Asn Gly Ile Asn Val
        210
```

( 2 ) INFORMATION FOR SEQ ID NO:13:

( i ) SEQUENCE CHARACTERISTICS:

(A) LENGTH: 2061 base pairs
(B) TYPE: nucleic acid
(C) STRANDEDNESS: unknown
(D) TOPOLOGY: unknown (ii) MOLECULE TYPE: DNA (genomic)

(ix) FEATURE:
(A) NAME/KEY: CDS
(B) LOCATION: 618..1775
(D) OTHER INFORMATION: /note="This corresponds to the entire methylase"

(xi) SEQUENCE DESCRIPTION: SEQ ID NO: 13:

```
GGATCTCTAT CGCGCAAAGT CAAAGGAAGA AGATATCACG GTTGAGAACG AAATCACAAA          60

GGAAAAATTC CCCATCAGCC TCAAGGCTTA TGGGGATGGT CCACTACAGC TTTCAACTGA         120

CAAAAATTTT TTGATGTACC CTCTTCTTGA GGAAATTGGG GCGTTCATCA ATGCCAAAGA         180

AAAAATAGAA GAAATTTTTG CCAATGAAGC ATTTCGTGC  TTCAGCGAAA TAAATGTCCT         240

ACCCTTGATA TACGATGAGA AGAGGCAGCG ATGTAATATT TTGGTTTTCG ATGCCGCACG         300

TGCCAGAGCT GAAACAGCTT ACATTCGCAA AGAAACAGAG GGGTCAGGAC GAAAACACCC         360

GGCTTACAGA TTTTTTGACA AAAATAAAAA TTACATCTGC GAAGTGCGCT ACGGGAATGC         420

TGCGGCAAAT GCGCTCCAAC GAGGACTTTG GACAAACACA AAAAATGCTA CATCATTTTT         480

TGATAGTGTA ACAAACGGCT GGGTTGATTA CTCTCATAAC TTGGTCTTAG TTAAGCTGCT         540

TTCGCACGCT TTGGTTTCAA GTCGCAAAGG CCACGAAGCT GCACTGGAAG AGATCAAGAA         600
```

| | | | | | | | | | | | | |
|---|---|---|---|---|---|---|---|---|---|---|---|---|
| AGACATCCTG | CAACTA | AGC | AAA | CGA | ATG | GGA | TCA | ATG | TTT | AAC | ACC | ACA | 650 |
| | | Ser | Lys | Arg | Met | Gly | Ser | Met | Phe | Asn | Thr | Thr | |
| | | 1 | | | 5 | | | | | 10 | | | |
| CAA | CCA | TTG | TTT | GAA | AAA | GTA | ATT | TTA | GAC | ACT | CCG | GAA | ACT | CAA | GGA | 698 |
| Gln | Pro | Leu | Phe | Glu | Lys | Val | Ile | Leu | Asp | Thr | Pro | Glu | Thr | Gln | Gly | |
| | | | 15 | | | | 20 | | | | | 25 | | | | |
| ATA | AAA | TAT | GCC | GGA | TCA | AAA | CTA | AAA | TTG | ATC | CAA | CAC | ATT | TTA | TCC | 746 |
| Ile | Lys | Tyr | Ala | Gly | Ser | Lys | Leu | Lys | Leu | Ile | Gln | His | Ile | Leu | Ser | |
| | | 30 | | | | | 35 | | | | | 40 | | | | |
| CTA | CTT | GAC | AAC | CTA | GAT | GTA | AAA | ACC | GTA | TTC | GAT | GGA | TTT | TCT | GGA | 794 |
| Leu | Leu | Asp | Asn | Leu | Asp | Val | Lys | Thr | Val | Phe | Asp | Gly | Phe | Ser | Gly | |
| | | 45 | | | | 50 | | | | | 55 | | | | | |
| ACT | ACT | AGG | GTC | TCG | CAG | GCC | TTG | GCG | AAG | TGC | GGA | TTT | CAT | GTC | ACC | 842 |
| Thr | Thr | Arg | Val | Ser | Gln | Ala | Leu | Ala | Lys | Cys | Gly | Phe | His | Val | Thr | |
| 60 | | | | | 65 | | | | | 70 | | | | | 75 | |
| AGC | AAC | GAC | ATT | TCA | GAT | TGG | TCT | TAT | GTA | TTT | GGC | TTG | TGC | TAC | CTA | 890 |
| Ser | Asn | Asp | Ile | Ser | Asp | Trp | Ser | Tyr | Val | Phe | Gly | Leu | Cys | Tyr | Leu | |
| | | | | 80 | | | | | 85 | | | | | 90 | | |
| AAA | AAC | AAA | AAA | CAC | CCC | AAC | GAA | TAC | AAG | GAA | CTA | ATT | GAA | CAC | CTT | 938 |
| Lys | Asn | Lys | Lys | His | Pro | Asn | Glu | Tyr | Lys | Glu | Leu | Ile | Glu | His | Leu | |
| | | | 95 | | | | | 100 | | | | | 105 | | | |
| AAC | TCA | ATA | AAT | GGC | TAC | GAC | GGT | TGG | TTC | ACT | GAG | AAG | TAT | GGC | GGC | 986 |
| Asn | Ser | Ile | Asn | Gly | Tyr | Asp | Gly | Trp | Phe | Thr | Glu | Lys | Tyr | Gly | Gly | |
| | | 110 | | | | | 115 | | | | | 120 | | | | |
| CTT | GAC | TAT | TCA | GGC | AGT | GCT | ATT | CAA | CCT | GAC | GGC | ACA | AAA | AAA | CCT | 1034 |
| Leu | Asp | Tyr | Ser | Gly | Ser | Ala | Ile | Gln | Pro | Asp | Gly | Thr | Lys | Lys | Pro | |
| | | 125 | | | | 130 | | | | | 135 | | | | | |
| TGG | CAA | GTC | CAC | AAT | ACG | CGG | AAG | CTA | GAT | GGG | ATC | CGC | GAC | GAA | ATA | 1082 |
| Trp | Gln | Val | His | Asn | Thr | Arg | Lys | Leu | Asp | Gly | Ile | Arg | Asp | Glu | Ile | |
| 140 | | | | | 145 | | | | | 150 | | | | | 155 | |
| GAT | TCA | TTA | TCA | CTG | AAT | GAA | ACC | GAA | AAA | GCC | GTC | GCC | CTT | ACC | AGT | 1130 |
| Asp | Ser | Leu | Ser | Leu | Asn | Glu | Thr | Glu | Lys | Ala | Val | Ala | Leu | Thr | Ser | |
| | | | | 160 | | | | | 165 | | | | | 170 | | |
| TTA | ATT | TTA | GCA | ATG | GAC | GAA | GTC | GAC | AAC | ACA | CTT | GGC | CAC | TTC | ACT | 1178 |

```
            Leu  Ile  Leu  Ala  Met  Asp  Glu  Val  Asp  Asn  Thr  Leu  Gly  His  Phe  Thr
                           175                     180                      185

TCA  TAC  CTA  AAA  GAA  TGG  TCC  CCT  CGA  TCA  TTC  AAA  GAA  ATG  CGA  ATG              1226
Ser  Tyr  Leu  Lys  Glu  Trp  Ser  Pro  Arg  Ser  Phe  Lys  Glu  Met  Arg  Met
          190                     195                     200

AAA  ATC  CCA  AAA  ATA  TTT  ATT  AAC  TCC  GAA  GAC  AAC  CAA  GTA  TTA  AAA              1274
Lys  Ile  Pro  Lys  Ile  Phe  Ile  Asn  Ser  Glu  Asp  Asn  Gln  Val  Leu  Lys
     205                     210                     215

GGC  GAT  ATA  TTC  GCA  TCA  ATG  ACT  AAC  ATC  AAT  GTC  GAT  TTT  GCT  TAC              1322
Gly  Asp  Ile  Phe  Ala  Ser  Met  Thr  Asn  Ile  Asn  Val  Asp  Phe  Ala  Tyr
220                      225                     230                     235

TTT  GAT  CCA  CCT  TAC  GGT  TCA  AAC  AAC  GAA  AAG  ATG  CCT  CCT  TCG  CGA              1370
Phe  Asp  Pro  Pro  Tyr  Gly  Ser  Asn  Asn  Glu  Lys  Met  Pro  Pro  Ser  Arg
                    240                     245                     250

GTA  CGC  TAT  GCA  TCG  TAT  TAT  CAT  TTA  TGG  ACA  ACT  ATA  TGC  AAG  AAT              1418
Val  Arg  Tyr  Ala  Ser  Tyr  Tyr  His  Leu  Trp  Thr  Thr  Ile  Cys  Lys  Asn
               255                     260                     265

GAT  AAG  CCG  AGC  ATT  TTC  GGA  GCC  GCA  GGC  AGA  AGA  TTA  GAT  ACA  TCA              1466
Asp  Lys  Pro  Ser  Ile  Phe  Gly  Ala  Ala  Gly  Arg  Arg  Leu  Asp  Thr  Ser
          270                     275                     280

GAT  AAA  ATT  GCA  GCA  ACC  GTT  TTT  GAA  GAG  TTT  CGA  AAA  GAT  GAT  GAT              1514
Asp  Lys  Ile  Ala  Ala  Thr  Val  Phe  Glu  Glu  Phe  Arg  Lys  Asp  Asp  Asp
     285                     290                     295

GGT  AAA  TTT  ATT  GCA  GTT  AAA  GCA  ATT  GAT  AAA  TTA  ATA  AAA  AAC  ATT              1562
Gly  Lys  Phe  Ile  Ala  Val  Lys  Ala  Ile  Asp  Lys  Leu  Ile  Lys  Asn  Ile
300                      305                     310                     315

CAA  GCA  CGA  TAT  GTT  GCC  CTT  TCC  TAC  AGT  TCG  GGC  GGA  AAA  GCC  ACT              1610
Gln  Ala  Arg  Tyr  Val  Ala  Leu  Ser  Tyr  Ser  Ser  Gly  Gly  Lys  Ala  Thr
                    320                     325                     330

GCC  GAG  GAG  CTA  GGC  GAA  ATA  CTT  AAC  CGC  CAC  GGA  AAA  ATT  ATA  AAA              1658
Ala  Glu  Glu  Leu  Gly  Glu  Ile  Leu  Asn  Arg  His  Gly  Lys  Ile  Ile  Lys
               335                     340                     345

ACA  ATT  GAA  GTT  GAT  CAC  AAG  CGA  AAT  GTC  ATG  GCA  GAA  ATG  AAG  TGG              1706
Thr  Ile  Glu  Val  Asp  His  Lys  Arg  Asn  Val  Met  Ala  Glu  Met  Lys  Trp
          350                     355                     360

ACC  AAT  GAG  TGG  CTT  AGG  GAT  GCA  GAA  GAG  CCA  AAT  CGA  GAG  TTT  ATT              1754
Thr  Asn  Glu  Trp  Leu  Arg  Asp  Ala  Glu  Glu  Pro  Asn  Arg  Glu  Phe  Ile
     365                     370                     375

TTT  CTC  ATT  GAA  AAA  AAT  TCC  TAACTGGGTG  GTCAAGCGAA  CGCCAACAAG                        1805
Phe  Leu  Ile  Glu  Lys  Asn  Ser
380                      385

GACCACGGCT  TCGCCGTTTT  TACGGTCCCT  GTTGGTGCCA  TTCACTCGCT  TCGCTCCTTC                        1865

CGGAGCCGTG  CTTGACACGG  CGATCGGCTT  TGGCCTGGTG  TCCGTGGCCG  CCGTGGCGGC                        1925

GGTGTTTGGA  AAATTTCTGC  TCGGCGGGTT  GCTGGCCGCA  TTGGCGCTGG  GCGTATTTGT                        1985

TCGTCTGAAG  CGCCGCACGA  AGTCCTGAGC  GTCTGCACGG  ACGCGTTGTT  CTCGATGTCG                        2045

AACTGCGGGG  CTCGAC                                                                            2061
```

( 2 ) INFORMATION FOR SEQ ID NO:14:

( i ) SEQUENCE CHARACTERISTICS:
        ( A ) LENGTH: 386 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 14:

```
Ser  Lys  Arg  Met  Gly  Ser  Met  Phe  Asn  Thr  Thr  Gln  Pro  Leu  Phe  Glu
  1             5                    10                      15
```

Lys Val Ile Leu Asp Thr Pro Glu Thr Gln Gly Ile Lys Tyr Ala Gly
            20                      25                      30

Ser Lys Leu Lys Leu Ile Gln His Ile Leu Ser Leu Leu Asp Asn Leu
        35                      40                      45

Asp Val Lys Thr Val Phe Asp Gly Phe Ser Gly Thr Thr Arg Val Ser
        50                      55                      60

Gln Ala Leu Ala Lys Cys Gly Phe His Val Thr Ser Asn Asp Ile Ser
65                      70                      75                      80

Asp Trp Ser Tyr Val Phe Gly Leu Cys Tyr Leu Lys Asn Lys Lys His
                    85                      90                      95

Pro Asn Glu Tyr Lys Glu Leu Ile Glu His Leu Asn Ser Ile Asn Gly
                100                     105                     110

Tyr Asp Gly Trp Phe Thr Glu Lys Tyr Gly Gly Leu Asp Tyr Ser Gly
            115                     120                     125

Ser Ala Ile Gln Pro Asp Gly Thr Lys Lys Pro Trp Gln Val His Asn
        130                     135                     140

Thr Arg Lys Leu Asp Gly Ile Arg Asp Glu Ile Asp Ser Leu Ser Leu
145                     150                     155                     160

Asn Glu Thr Glu Lys Ala Val Ala Leu Thr Ser Leu Ile Leu Ala Met
                165                     170                     175

Asp Glu Val Asp Asn Thr Leu Gly His Phe Thr Ser Tyr Leu Lys Glu
            180                     185                     190

Trp Ser Pro Arg Ser Phe Lys Glu Met Arg Met Lys Ile Pro Lys Ile
        195                     200                     205

Phe Ile Asn Ser Glu Asp Asn Gln Val Leu Lys Gly Asp Ile Phe Ala
    210                     215                     220

Ser Met Thr Asn Ile Asn Val Asp Phe Ala Tyr Phe Asp Pro Pro Tyr
225                     230                     235                     240

Gly Ser Asn Asn Glu Lys Met Pro Pro Ser Arg Val Arg Tyr Ala Ser
                245                     250                     255

Tyr Tyr His Leu Trp Thr Thr Ile Cys Lys Asn Asp Lys Pro Ser Ile
            260                     265                     270

Phe Gly Ala Ala Gly Arg Arg Leu Asp Thr Ser Asp Lys Ile Ala Ala
        275                     280                     285

Thr Val Phe Glu Glu Phe Arg Lys Asp Asp Asp Gly Lys Phe Ile Ala
    290                     295                     300

Val Lys Ala Ile Asp Lys Leu Ile Lys Asn Ile Gln Ala Arg Tyr Val
305                     310                     315                     320

Ala Leu Ser Tyr Ser Ser Gly Gly Lys Ala Thr Ala Glu Glu Leu Gly
                325                     330                     335

Glu Ile Leu Asn Arg His Gly Lys Ile Ile Lys Thr Ile Glu Val Asp
            340                     345                     350

His Lys Arg Asn Val Met Ala Glu Met Lys Trp Thr Asn Glu Trp Leu
        355                     360                     365

Arg Asp Ala Glu Glu Pro Asn Arg Glu Phe Ile Phe Leu Ile Glu Lys
    370                     375                     380

Asn Ser
385

( 2 ) INFORMATION FOR SEQ ID NO: 15:

( i ) SEQUENCE CHARACTERISTICS:
( A ) LENGTH: 209 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
    ( A ) NAME/KEY: CDS
    ( B ) LOCATION: 1..209

( x i ) SEQUENCE DESCRIPTION: SEQ ID NO: 15:

```
ATG TCC AAA GCA GCC TAC CAA GAT TTC ACA AAA AGA TTC TCC CTG CTA        48
Met Ser Lys Ala Ala Tyr Gln Asp Phe Thr Lys Arg Phe Ser Leu Leu
 1           5                   10                  15

ATA AAA AAA CAT CCA AAC CTC ATA ACG ATG ACA CTG AGC AAC ATT TTC        96
Ile Lys Lys His Pro Asn Leu Ile Thr Met Thr Leu Ser Asn Ile Phe
            20                  25                  30

ACA ATG CGA CTC ATT GGC AAC AAA ACC CAC GGC GAC TTG GCT GAG ATT       144
Thr Met Arg Leu Ile Gly Asn Lys Thr His Gly Asp Leu Ala Glu Ile
        35                  40                  45

GCG ATC TCC GAA TTC ATT AAT CAG TAC ATG TAT GAC TTT AAG TCA ATT       192
Ala Ile Ser Glu Phe Ile Asn Gln Tyr Met Tyr Asp Phe Lys Ser Ile
    50                  55                  60

CAT GTC GGC AAA GAT CT                                                 209
His Val Gly Lys Asp
 65
```

( 2 ) INFORMATION FOR SEQ ID NO: 16:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 16:

```
Met Ser Lys Ala Ala Tyr Gln Asp Phe Thr Lys Arg Phe Ser Leu Leu
 1           5                   10                  15

Ile Lys Lys His Pro Asn Leu Ile Thr Met Thr Leu Ser Asn Ile Phe
            20                  25                  30

Thr Met Arg Leu Ile Gly Asn Lys Thr His Gly Asp Leu Ala Glu Ile
        35                  40                  45

Ala Ile Ser Glu Phe Ile Asn Gln Tyr Met Tyr Asp Phe Lys Ser Ile
    50                  55                  60

His Val Gly Lys Asp
 65
```

( 2 ) INFORMATION FOR SEQ ID NO: 17:

( i ) SEQUENCE CHARACTERISTICS:
        ( A ) LENGTH: 209 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..209

( x i ) SEQUENCE DESCRIPTION: SEQ ID NO: 17:

```
ATG TCG AAA GCA GCA TAT CAA GAT TTC ACA AAA AGA TTC TCC CTG CTA        48
Met Ser Lys Ala Ala Tyr Gln Asp Phe Thr Lys Arg Phe Ser Leu Leu
 1           5                   10                  15

ATA AAA AAA CAT CCA AAC CTC ATA ACG ATG ACA CTG AGC AAC ATT TTC        96
Ile Lys Lys His Pro Asn Leu Ile Thr Met Thr Leu Ser Asn Ile Phe
            20                  25                  30
```

```
ACA ATG CGA CTC ATT GGC AAC AAA ACC CAC GGC GAC TTG GCT GAG ATT        144
Thr Met Arg Leu Ile Gly Asn Lys Thr His Gly Asp Leu Ala Glu Ile
         35                  40                  45

GCG ATC TCC GAA TTC ATT AAT CAG TAC ATG TAT GAC TTT AAG TCA ATT        192
Ala Ile Ser Glu Phe Ile Asn Gln Tyr Met Tyr Asp Phe Lys Ser Ile
     50                  55                  60

CAT GTC GGC AAA GAT CT                                                 209
His Val Gly Lys Asp
 65
```

( 2 ) INFORMATION FOR SEQ ID NO: 18:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 18:

```
Met Ser Lys Ala Ala Tyr Gln Asp Phe Thr Lys Arg Phe Ser Leu Leu
 1               5                  10                  15

Ile Lys Lys His Pro Asn Leu Ile Thr Met Thr Leu Ser Asn Ile Phe
             20                  25                  30

Thr Met Arg Leu Ile Gly Asn Lys Thr His Gly Asp Leu Ala Glu Ile
         35                  40                  45

Ala Ile Ser Glu Phe Ile Asn Gln Tyr Met Tyr Asp Phe Lys Ser Ile
     50                  55                  60

His Val Gly Lys Asp
 65
```

( 2 ) INFORMATION FOR SEQ ID NO: 19:

( i ) SEQUENCE CHARACTERISTICS:
        ( A ) LENGTH: 209 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..209

( x i ) SEQUENCE DESCRIPTION: SEQ ID NO: 19:

```
ATG TCC AAA GCA GCC TAC CAA GAT TTC ACA AAA AGA TTC TCC CTG CTA         48
Met Ser Lys Ala Ala Tyr Gln Asp Phe Thr Lys Arg Phe Ser Leu Leu
 1               5                  10                  15

ATA AAA AAA CAT CCA AAC CTC ATA ACG ATG ACA CTG AGC AAC ATT TTC         96
Ile Lys Lys His Pro Asn Leu Ile Thr Met Thr Leu Ser Asn Ile Phe
             20                  25                  30

ACA ATG CGA CTC ATT GGC AAC AAA ACC CAC GGC GAC TTG GCT GAG ATT        144
Thr Met Arg Leu Ile Gly Asn Lys Thr His Gly Asp Leu Ala Glu Ile
         35                  40                  45

GCG ATC TCC GAA TTC ATT AAT CAG TAC ATG TAT GAC TTT AAG TCA ATT        192
Ala Ile Ser Glu Phe Ile Asn Gln Tyr Met Tyr Asp Phe Lys Ser Ile
     50                  55                  60

CAT GTC GGC AAA GAT CT                                                 209
His Val Gly Lys Asp
 65
```

( 2 ) INFORMATION FOR SEQ ID NO: 20:

( i ) SEQUENCE CHARACTERISTICS:
 ( A ) LENGTH: 69 amino acids
 ( B ) TYPE: amino acid
 ( D ) TOPOLOGY: linear ( i i ) MOLECULE TYPE: protein ( x i ) SEQUENCE DESCRIPTION: SEQ ID NO: 20:

```
Met Ser Lys Ala Ala Tyr Gln Asp Phe Thr Lys Arg Phe Ser Leu Leu
 1               5                  10                     15

Ile Lys Lys His Pro Asn Leu Ile Thr Met Thr Leu Ser Asn Ile Phe
             20                  25                  30

Thr Met Arg Leu Ile Gly Asn Lys Thr His Gly Asp Leu Ala Glu Ile
         35                  40                  45

Ala Ile Ser Glu Phe Ile Asn Gln Tyr Met Tyr Asp Phe Lys Ser Ile
     50                  55                  60

His Val Gly Lys Asp
 65
```

( 2 ) INFORMATION FOR SEQ ID NO: 21:

( i ) SEQUENCE CHARACTERISTICS:
  ( A ) LENGTH: 209 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i x ) FEATURE:
  ( A ) NAME/KEY: CDS
  ( B ) LOCATION: 1..209

( x i ) SEQUENCE DESCRIPTION: SEQ ID NO: 21:

```
ATG TCG AAA GCA GCC TAC CAA GAT TTC ACA AAA AGA TTC TCC CTG CTA      48
Met Ser Lys Ala Ala Tyr Gln Asp Phe Thr Lys Arg Phe Ser Leu Leu
 1               5                  10                     15

ATA AAA AAA CAT CCA AAC CTC ATA ACG ATG ACA CTG AGC AAC ATT TTC      96
Ile Lys Lys His Pro Asn Leu Ile Thr Met Thr Leu Ser Asn Ile Phe
             20                  25                  30

ACA ATG CGA CTC ATT GGC AAC AAA ACC CAC GGC GAC TTG GCT GAG ATT     144
Thr Met Arg Leu Ile Gly Asn Lys Thr His Gly Asp Leu Ala Glu Ile
         35                  40                  45

GCG ATC TCC GAA TTC ATT AAT CAG TAC ATG TAT GAC TTT AAG TCA ATT     192
Ala Ile Ser Glu Phe Ile Asn Gln Tyr Met Tyr Asp Phe Lys Ser Ile
     50                  55                  60

CAT GTC GGC AAA GAT CT                                              209
His Val Gly Lys Asp
 65
```

( 2 ) INFORMATION FOR SEQ ID NO: 22:

( i ) SEQUENCE CHARACTERISTICS:
  ( A ) LENGTH: 69 amino acids
  ( B ) TYPE: amino acid
  ( D ) TOPOLOGY: linear ( i i ) MOLECULE TYPE: protein ( x i ) SEQUENCE DESCRIPTION: SEQ ID NO: 22:

```
Met Ser Lys Ala Ala Tyr Gln Asp Phe Thr Lys Arg Phe Ser Leu Leu
 1               5                  10                     15

Ile Lys Lys His Pro Asn Leu Ile Thr Met Thr Leu Ser Asn Ile Phe
             20                  25                  30

Thr Met Arg Leu Ile Gly Asn Lys Thr His Gly Asp Leu Ala Glu Ile
```

```
                35                      40                       45
Ala  Ile  Ser  Glu  Phe  Ile  Asn  Gln  Tyr  Met  Tyr  Asp  Phe  Lys  Ser  Ile
           50                      55                       60
His  Val  Gly  Lys  Asp
 65
```